United States Patent
Okuyama et al.

(10) Patent No.: US 9,733,265 B2
(45) Date of Patent: Aug. 15, 2017

(54) METHOD FOR ADJUSTING POSITION OF ASPIRATOR AND SAMPLE PROCESSING APPARATUS

(71) Applicant: Sysmex Corporation, Kobe-shi, Hyogo (JP)

(72) Inventors: Takeo Okuyama, Kobe (JP); Shoichiro Asada, Kobe (JP); Tsukasa Hirata, Kobe (JP); Kazuki Asao, Kobe (JP)

(73) Assignee: Sysmex Corporation (JP)

(*) Notice: Subject to any disclaimer, the term of this patent is extended or adjusted under 35 U.S.C. 154(b) by 80 days.

(21) Appl. No.: 14/527,100

(22) Filed: Oct. 29, 2014

(65) Prior Publication Data

US 2015/0114140 A1    Apr. 30, 2015

(30) Foreign Application Priority Data

Oct. 31, 2013 (JP) ................. 2013-227671

(51) Int. Cl.
*G01F 19/00* (2006.01)
*G01F 25/00* (2006.01)
*G01N 35/10* (2006.01)

(52) U.S. Cl.
CPC ..... *G01N 35/1011* (2013.01); *G01N 35/1016* (2013.01); *G01N 2035/1025* (2013.01)

(58) Field of Classification Search
CPC .......... G01N 35/1011; G01N 35/1016; G01N 2035/1025; A01B 12/006; B01L 2200/148; G01F 25/0092
USPC ................................. 73/1.74, 1.79
See application file for complete search history.

(56) References Cited

U.S. PATENT DOCUMENTS

| | | | | |
|---|---|---|---|---|
| 4,912,976 A | * | 4/1990 | Labriola, II | G01F 23/263 141/95 |
| 2002/0188379 A1 | * | 12/2002 | McGee | B25J 9/1692 700/245 |
| 2009/0133511 A1 | * | 5/2009 | Heinze | G01F 23/2962 73/863.01 |
| 2012/0065912 A1 | * | 3/2012 | Corkan | G01N 35/1011 702/94 |

(Continued)

FOREIGN PATENT DOCUMENTS

| | | |
|---|---|---|
| DE | 10 2008 058065 A1 | 5/2010 |
| EP | 0 681 184 A1 | 11/1995 |

(Continued)

OTHER PUBLICATIONS

Translation of EP 681184.*

*Primary Examiner* — Helen Kwok
*Assistant Examiner* — Nashmiya Fayyaz
(74) *Attorney, Agent, or Firm* — Brinks Gilson & Lione

(57) ABSTRACT

Disclosed is a method for adjusting a position of an aspirator in a sample processing apparatus, the sample processing apparatus comprising the aspirator configured to aspirate a sample or a reagent from a container and a capacitance sensor connected to the aspirator to detect change in capacitance, the method comprising: moving the aspirator above a position adjustment part which is electrically conductive and which is disposed at a predetermined position; obtaining capacitance detected by the capacitance sensor while moving the aspirator; and setting reference position information indicating a reference position of the aspirator based on change in the obtained capacitance.

16 Claims, 15 Drawing Sheets

(56) References Cited

U.S. PATENT DOCUMENTS

2013/0345894 A1* 12/2013 Haddad .............. G01N 35/1011
    700/302

FOREIGN PATENT DOCUMENTS

| EP | 1 767 950 A1 | 3/2007 |
|----|--------------|--------|
| JP | 2009-300152 A | 12/2009 |
| JP | 2010-249601 A | 11/2010 |
| JP | 2012-242106 A | 12/2012 |

* cited by examiner

F I G. 9
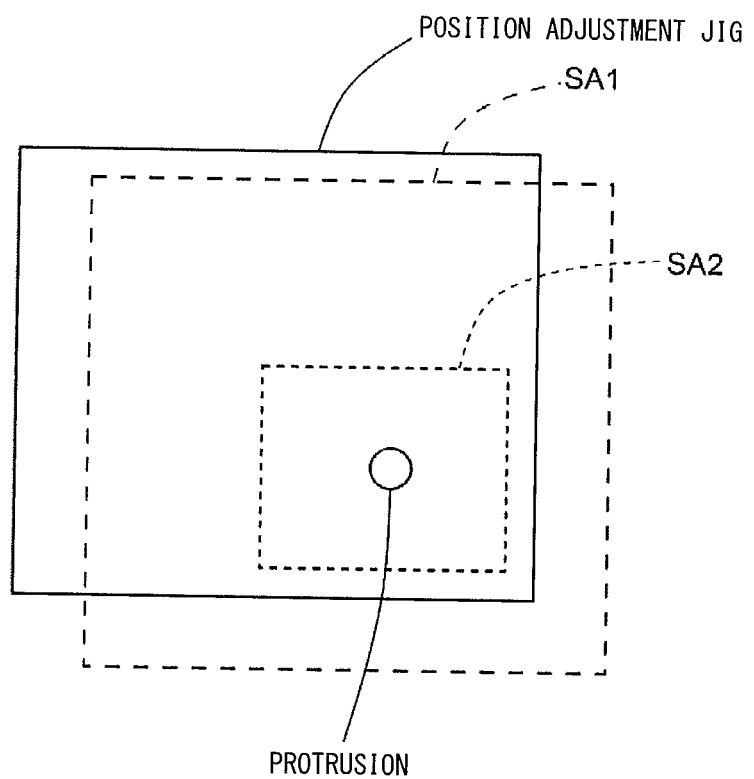

F I G. 1 4
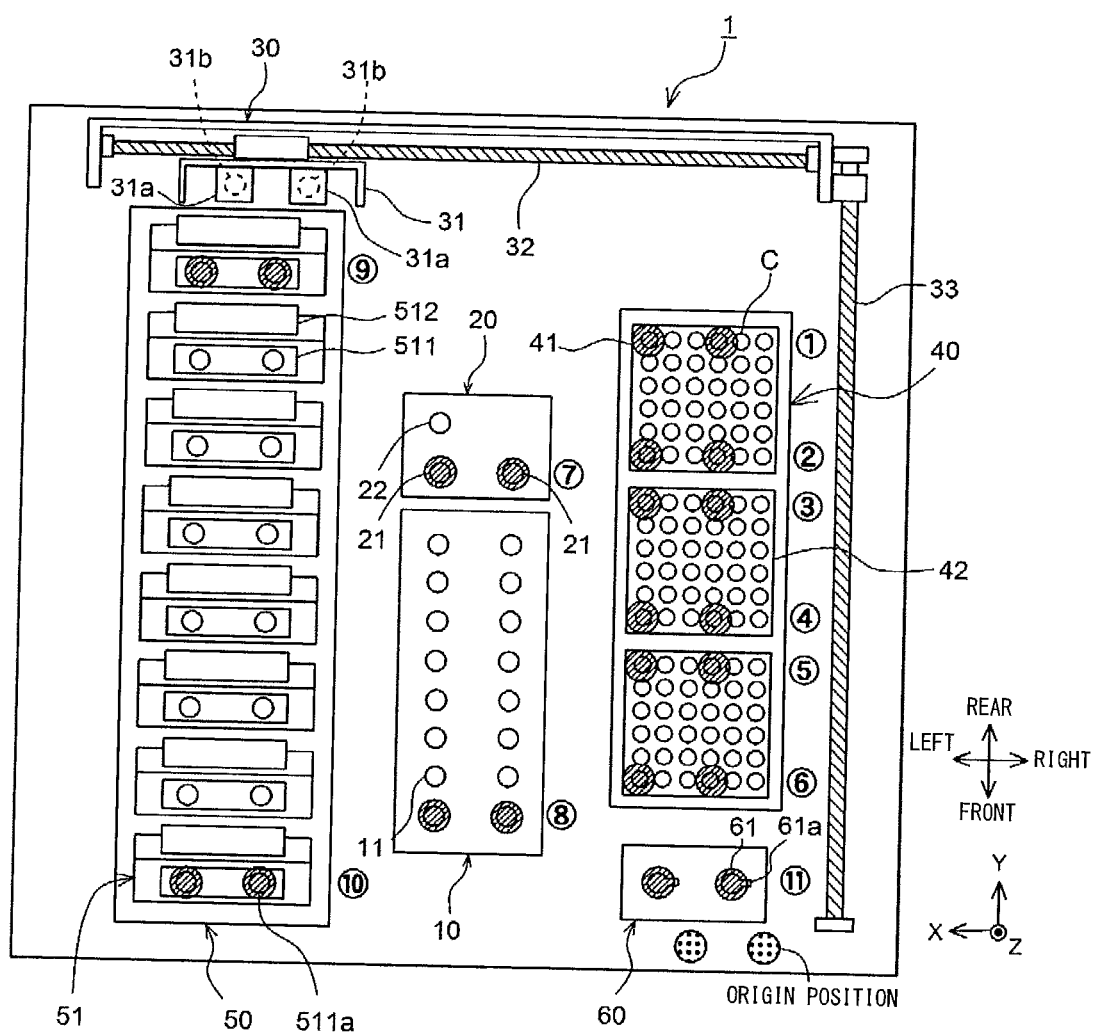

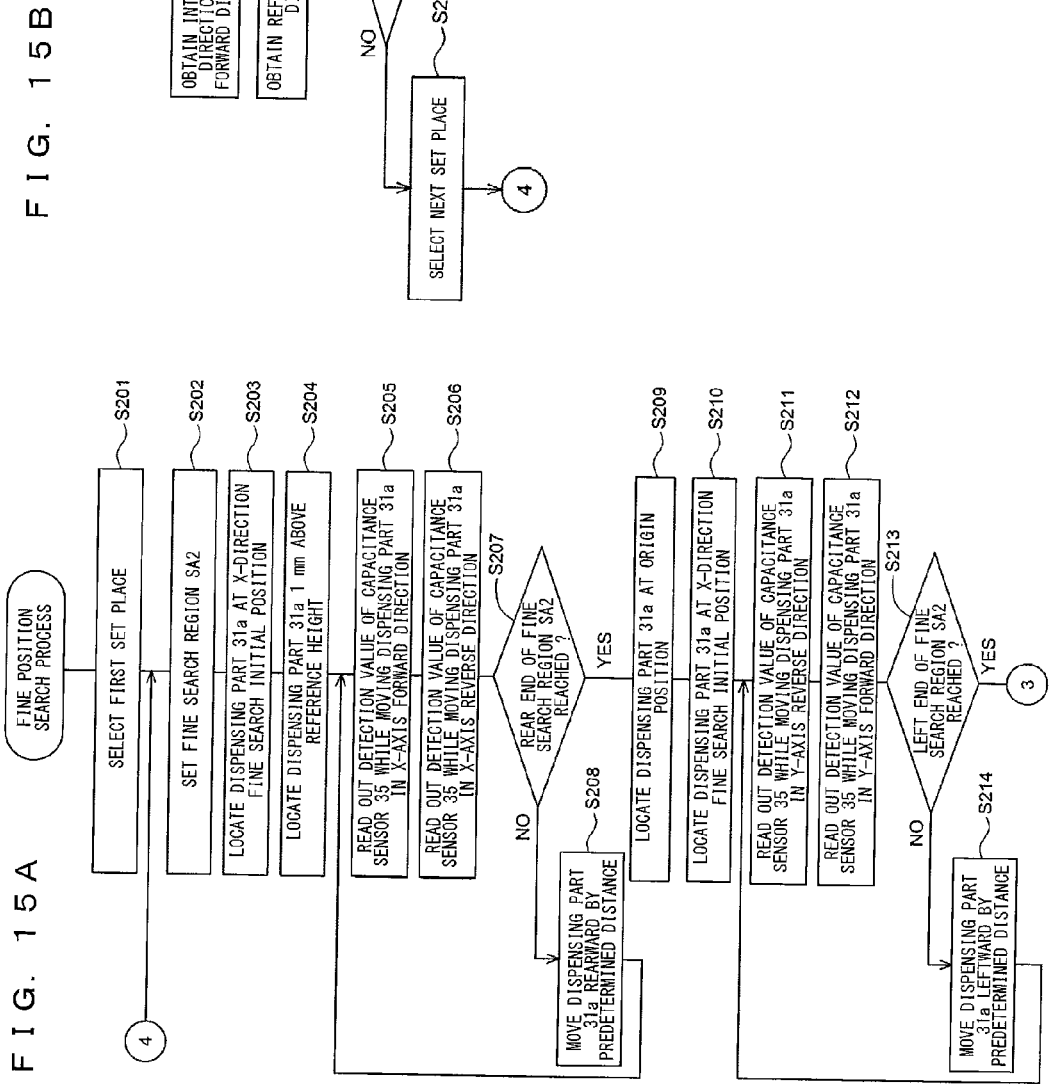

METHOD FOR ADJUSTING POSITION OF ASPIRATOR AND SAMPLE PROCESSING APPARATUS

RELATED APPLICATIONS

This application claims priority under 35 U.S.C. §119 to Japanese Patent Application No. 2013-227671 filed on Oct. 31, 2013, the entire content of which is hereby incorporated by reference.

FIELD OF THE INVENTION

The present invention relates to a method for adjusting the position of an aspirator which aspirates a sample collected from a subject, and a sample processing apparatus which uses the method for adjusting the position.

BACKGROUND OF THE INVENTION

There have been known sample processing apparatuses such as blood cell analyzers, urine particle analyzers, blood coagulation measuring apparatuses, immune analyzers, biochemical analyzers, nucleic acid amplification detecting apparatuses, and smear preparing apparatuses. Such a sample processing apparatus includes an aspiration tube for aspirating a sample or a reagent. The sample processing apparatus is configured to locate this aspiration tube above a sample container or a reagent container, and then to lower the aspiration tube to insert the aspiration tube into the sample container or the reagent container, thereby to aspirate the sample or the reagent.

In production of such a sample processing apparatus, dimensional variation may occur in dimensions of parts to be used when the parts are produced, mounting dimensions when the parts are assembled, and the like. This makes it difficult to accurately locate the aspiration tube above a sample container or a reagent container. In such a sample processing apparatus, if the aspiration tube cannot be accurately located, there is a risk that the aspiration tube may collide with a sample container, a reagent container, the apparatus body, or the like, causing poor aspiration or damage of the aspiration tube.

Japanese Laid-Open Patent Publication No. H11-160326 discloses a dispenser that can adjust the position of a nozzle (aspiration tube). The dispenser disclosed in Japanese Laid-Open Patent Publication No. H11-160326 includes a tip attachment part to which a nozzle tip is detachably attached. Between this tip attachment part and a dispensing pump, a jamming detection part is provided. In the dispenser, a positioning detection member having an insertion hole formed therein is disposed. When the position of the nozzle is to be adjusted, the tip attachment part (nozzle) having the nozzle tip attached thereto is lowered from above the positioning detection member, and whether the nozzle has collided with the positioning detection member is detected by the jamming detection part. When the leading end of the nozzle has entered the insertion hole, the nozzle does not collide with the positioning detection member. When the leading end of the nozzle goes outside the insertion hole, the nozzle collides with the positioning detection member. Such detection of presence or absence of collision is performed at a plurality of points while the position in the horizontal direction is being shifted. Thus, the position in the horizontal direction of the nozzle is corrected.

However, in the dispenser disclosed in Japanese Laid-Open Patent Publication No. H11-160326, in order to adjust the position in the horizontal direction of the nozzle, the nozzle is caused to collide with the positioning detection member a plurality of times. Thus, there is a risk that the nozzle is deformed or damaged, or the nozzle tip comes off the tip attachment part.

SUMMARY OF THE INVENTION

The scope of the present invention is defined solely by the appended claims, and is not affected to any degree by the statements within this summary.

A method for adjusting a position of an aspirator according to one aspect of described above is a method for adjusting a position of an aspirator in a sample processing apparatus, the sample processing apparatus including the aspirator configured to aspirate a sample or a reagent from a container and a capacitance sensor connected to the aspirator, the method including: moving the aspirator above a position adjustment part which is electrically conductive and which is disposed at a predetermined position; obtaining capacitance detected by the capacitance sensor while moving the aspirator; and setting reference position information indicating a reference position of the aspirator based on change in the obtained capacitance.

A sample processing apparatus according to one aspect of the present invention is a sample processing apparatus including: a liquid aspirator configured to aspirate a liquid from a container containing the liquid; a capacitance sensor connected to the aspirator; a movement mechanism connected to the liquid aspirator to move the aspirator; a position adjustment part which is disposed at a predetermined position and is electrically conductive; and a controller. The controller is programmed to perform operations comprising setting reference position information indicating a reference position of the liquid aspirator, based on change in capacitance detected by the capacitance sensor while the liquid aspirator is moving above the position adjustment part.

A sample processing apparatus according to another aspect of the present invention is a sample processing apparatus including: a liquid aspirator configured to aspirate a liquid from a container containing the liquid; a position adjustment part which is disposed at a predetermined position; a distance sensor connected to the liquid aspirator and configured to be able to detect change in a distance between the liquid aspirator and the position adjustment part in a non-contact manner; a movement mechanism connected to the liquid aspirator to move the liquid aspirator; and a controller. The controller is programmed to perform operations comprising: setting reference position information indicating a reference position of the liquid aspirator based on a result of detection by the sensor while the liquid aspirator is moving above the position adjustment part disposed at a predetermined position.

BRIEF DESCRIPTION OF THE DRAWINGS

FIG. 9 is a schematic diagram for explaining the outline of search of the position of a protrusion;

FIG. 14 is a plan view of the inside of the sample processing apparatus for explaining the order of position adjustment in a fine position search process;

FIG. 15A is a flow chart (first half) showing the procedure of the fine position search process; and FIG. 15B is the flow chart (second half) showing the procedure of the fine position search process.

DETAILED DESCRIPTION OF THE PREFERRED EMBODIMENTS

Hereinafter, a sample processing apparatus 1 according to the present embodiment will be described with reference to the drawings.

<Structure of Sample Processing Apparatus>

Figure 1:
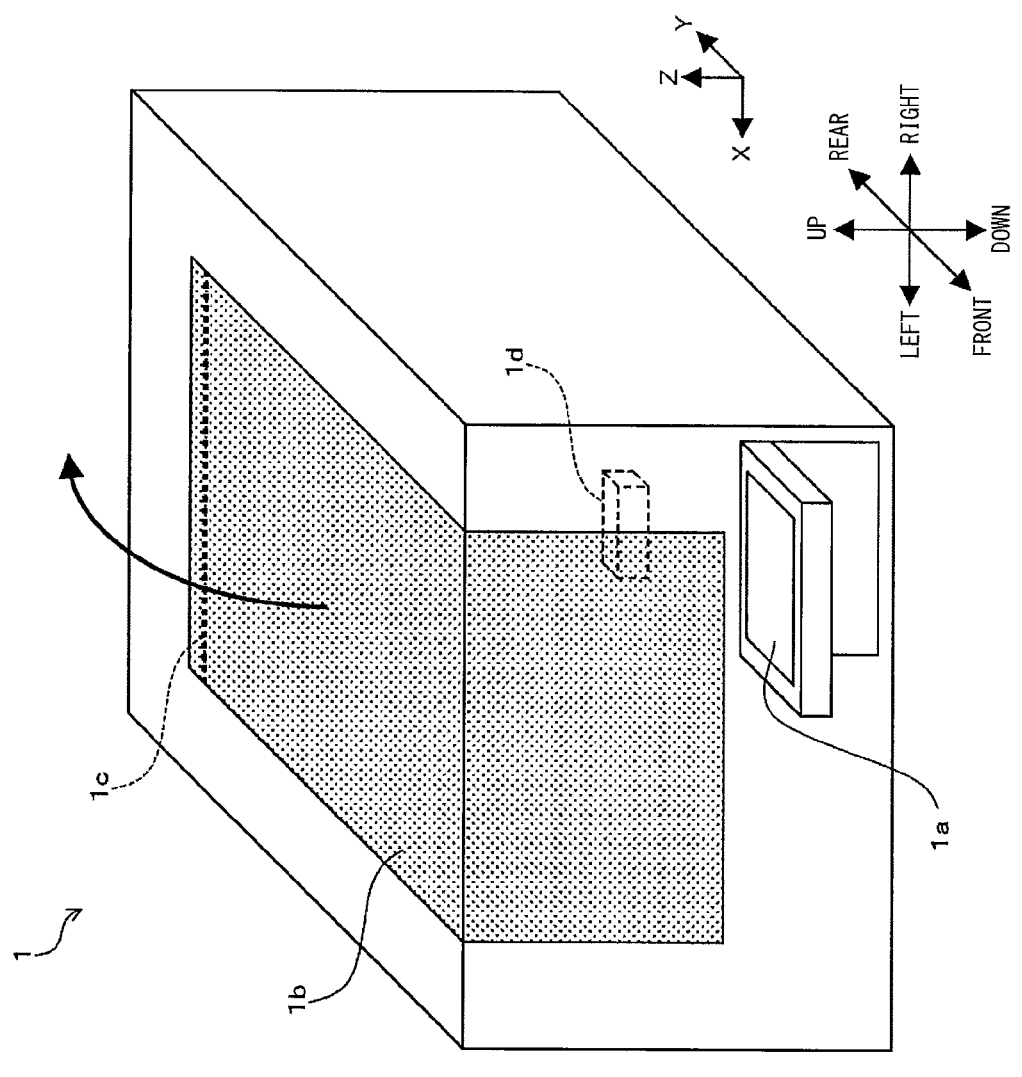
FIG. 1 is a schematic perspective view showing an external structure of a sample processing apparatus according to an embodiment.

Hereinafter, a structure of a sample processing apparatus according to the present embodiment will be described. FIG. 1 is a schematic perspective view showing an external structure of the sample processing apparatus 1.

The sample processing apparatus 1 is an apparatus that performs detection by: using a cancer-derived mRNA present in an excised tissue, to amplify nucleic acid by LAMP (Loop-mediated Isothermal Amplification); and measuring turbidity of the solution occurring associated with the amplification. Details of the LAMP method are disclosed in U.S. Pat. No. 6,410,278.

The sample processing apparatus 1 includes a display input unit 1a composed of a touch panel, and a cover 1b extending from the front face to the top face. The cover 1b is configured to be able to rotate about a shaft 1c. The cover 1b is switched between a locked state and an unlocked state by a lock mechanism 1d. While the cover 1b is in an unlocked state, an operator opens an upper portion of the sample processing apparatus 1 by rotating the cover 1b upward from the state shown in FIG. 1, thereby being able to access the inside of the sample processing apparatus 1.

Figure 2:
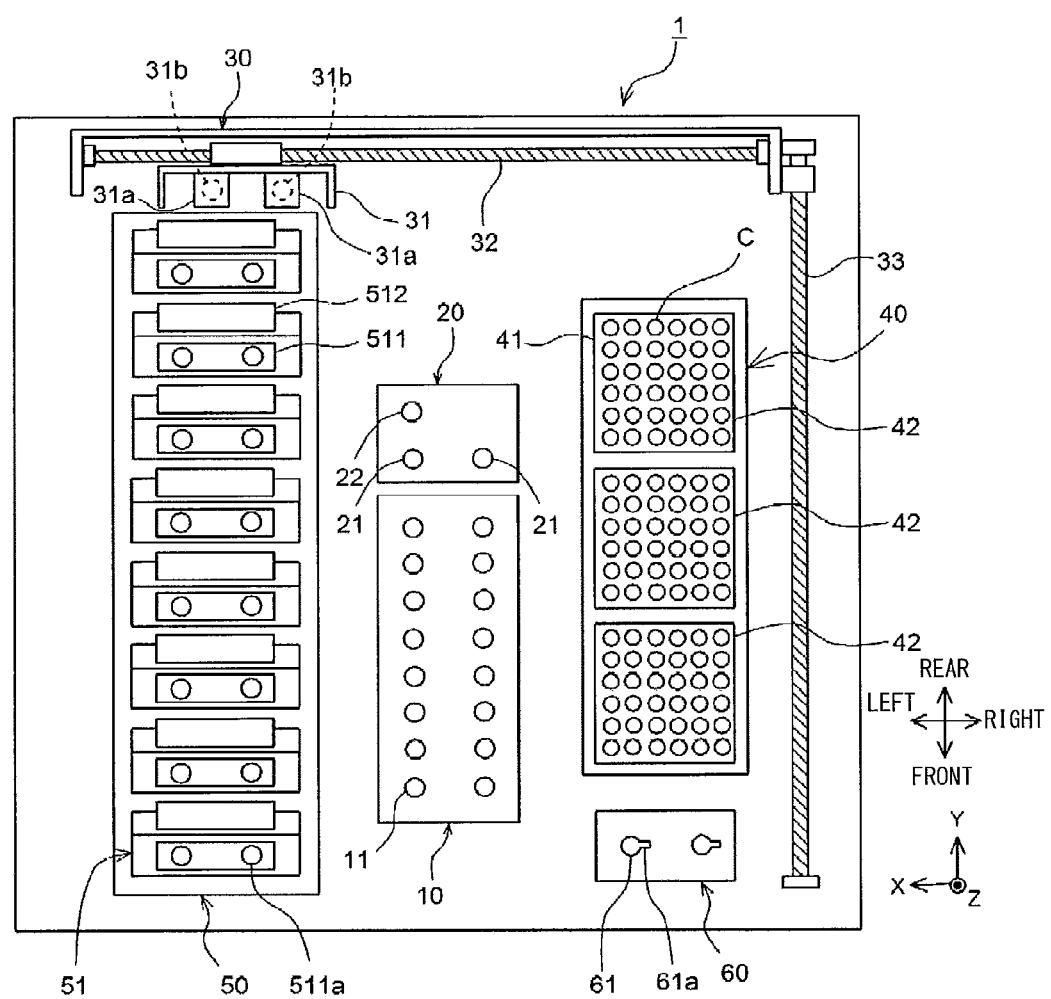
FIG. 2 is a schematic plan view showing a structure of the inside of the sample processing apparatus according to the embodiment.

FIG. 2 is a schematic plan view showing a structure of the inside of the sample processing apparatus 1.

The sample processing apparatus 1 includes, inside thereof, a sample container setting part 10, a reagent container setting part 20, dispensing parts 31a, a movement mechanism 30, a tip setting part 40, a reaction part 50, and a tip disposal part 60.

The tip setting part 40 and the tip disposal part 60 are provided on the right side in the sample processing apparatus 1. The tip setting part 40 and the tip disposal part 60 are arranged side by side in the front-rear direction such that the tip setting part 40 is on the rear side and the tip disposal part 60 is on the front side. The sample container setting part 10 and the reagent container setting part 20 are provided near the center in the left-right direction (X-axis direction) in the sample processing apparatus 1. The sample container setting part 10 and the reagent container setting part 20 are arranged side by side in the front-rear direction (Y-axis direction) such that the sample container setting part 10 is on the front side and the reagent container setting part 20 is on the rear side. The reaction part 50 is provided on the left side in the sample processing apparatus 1.

On the top face of the sample container setting part 10, 16 holding holes 11 each having an open top are formed. The holding holes 11 are arranged in two in the left-right direction and eight in the front-rear direction. Among these 16 holding holes 11, into two holding holes 11 that are on the rear-most side (i.e., two holding holes 11 adjacent to the reagent container setting part 20), two sample containers are set which respectively contain a control for confirming that nucleic acid that should be amplified is amplified normally and a control for confirming that nucleic acid that should not be amplified is not amplified normally.

In a holding hole 11, a sample container containing a solubilized extract (hereinafter, referred to as "sample") prepared by subjecting in advance an excised tissue to pretreatment (homogenization, centrifugation), or a sample container containing a diluted sample is set. As pretreatment for preparing a solubilized extract (specimen for nucleic acid amplification reaction) from an excised tissue, the method disclosed in US Patent Application Publication No. 2006/0121515 can be used. At this time, a sample container containing a sample prepared from one excised tissue and a sample container containing a diluted sample obtained by diluting the sample are set in holding holes 11 adjacent to each other in the left-right direction.

When a calibration curve is to be created, before a sample is measured (for example, immediately after activation of the apparatus), sample containers each containing a calibrator which includes a target nucleic acid at a predetermined concentration and based on which a calibration curve is to be created are set in predetermined holding holes 11. Also in this case, measurement is performed in the similar manner as in the measurement of the sample described later, and a calibration curve is created.

On the top face of the reagent container setting part 20, three holding holes 21 and 22 each having an open top are formed. More specifically, two holding holes 21 are provided so as to be arranged in the left-right direction on the front side. To the rear of the left holding hole 21 of the two holding holes 21, one holding hole 22 is provided. In the left front holding hole 21, a reagent container containing a primer reagent including a primer for cytokeratin 19 (CK19) is set. In the right front holding hole 21, a reagent container containing a primer reagent including a primer for β actin is set. In the rear holding hole 22, a reagent container is set that contains an enzyme reagent including an enzyme, for promoting nucleic acid amplification reaction, that is commonly used for nucleic acid amplification reaction of CK19 and nucleic acid amplification reaction of β actin. There are cases where sample measurement regarding β actin is not performed even when sample measurement regarding CK19 is performed. In such a case, the β actin primer reagent is not set in the right holding hole 21.

The movement mechanism 30 includes an arm part 31, a shaft 32 extending in the X-axis direction, a shaft 33 extending in the Y-axis direction, and stepping motors 32a, 33a, and 34a (see FIG. 5) for moving the arm part 31. The arm part 31, supported by the shaft 32, is movable in the X-axis direction, and a mechanism including the arm part 31 and the shaft 32, supported by the shaft 33, is movable in the Y-axis direction. To the arm part 31, two dispensing parts 31a independently movable in the up-down direction (Z-axis direction) relative to the arm part 31 are mounted. Each dispensing part 31a includes, at its lower end (end on the Z-axis negative direction side), a nozzle part 31b to which a pipette tip C is attached.

The tip setting part 40 is provided with three rack set parts 42 each capable of having a rack 41 set thereon, each rack 41 holding 36 pipette tips C therein. The arm part 31 of the movement mechanism 30 is moved in the X-axis direction and the Y-axis direction inside the sample processing apparatus 1, and each dispensing part 31a is moved in the Z-axis direction, whereby the pipette tip C is attached to the lower end of the nozzle part 31b.

Figure 3:
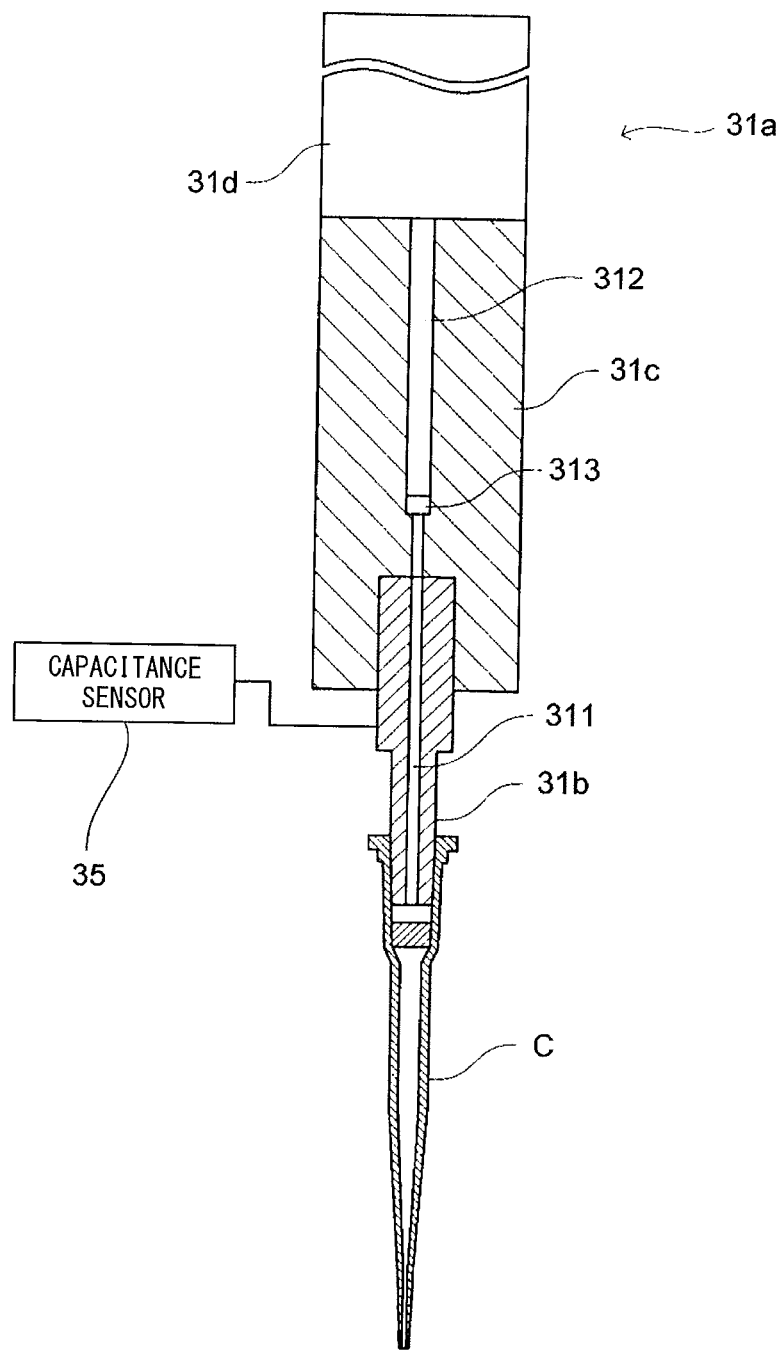
FIG. 3 is a side cross-sectional view showing a state where a pipette tip is attached to a nozzle part of a dispensing part.

FIG. 3 is a side cross-sectional view showing a state where a pipette tip C is attached to the nozzle part 31b of the dispensing part 31a. As shown in FIG. 3, with respect to the dispensing part 31a, the leading end of the nozzle part 31b is detachably fitted into an upper opening of the pipette tip C. On the upper side of the nozzle part 31b, a cylinder part 31c hermetically fixing the proximal end of the nozzle part 31b, and a piston driving part 31d connected to the cylinder part 31c are provided.

The nozzle part 31b has, along its axis, a through hole 311 which is in communication with the pipette tip C. The cylinder part 31c includes a cylinder hole 313 which is in communication with the through hole 311 and which houses a piston 312. The piston driving part 31d reciprocates the piston 312 in the cylinder hole 313, whereby a liquid is aspirated/discharged (dispensed) into/from the pipette tip C. By the amount of movement of the piston 312, the dispensing amount of the liquid is determined.

The dispensing part 31a is provided with a capacitance sensor 35. The capacitance sensor 35 is connected to the nozzle part 31b of the dispensing part 31. The nozzle part 31b functions as a probe (i.e., electrode) for the capacitance sensor 35. The pipette tip C is formed from electrically conductive plastic containing carbon. In a state where the pipette tip C is attached to the nozzle part 31b, the nozzle part 31b and the pipette tip C function as the electrode. Thus, change in capacitance at the time when the pipette tip C comes into contact with a liquid surface can be detected by the capacitance sensor 35, whereby the liquid surface can be detected.

Next, with reference to FIG. 2, the tip disposal part 60 will be described. The tip disposal part 60 includes two disposal holes 61. Each disposal hole 61 is provided with a cutout 61a extending sideways. Pipette tips C attached to the movement mechanism 30 are discarded into the tip disposal part 60 every time operation of aspirating and discharging a sample or a reagent ends. When the pipette tips C are to be discarded, the nozzle parts 31b having the pipette tips C attached thereto are inserted in disposal holes 61 of the tip disposal part 60, and the entirety of each pipette tip C is located below the top face of the tip disposal part 60 to be moved sideways, whereby the nozzle parts 31b are located at the cutouts 61a, respectively. Then, the dispensing parts 31a are moved upward, whereby the pipette tips C come into contact with the cutouts 61a, respectively, and the pipette tips C are detached from the nozzle parts 31b, respectively.

The reaction part 50 includes eight reaction detection blocks 51 arranged in the front-rear direction. Each of the eight reaction detection blocks 51 includes a reaction chamber setting part 511 and a cap closing mechanism 512.

In the top face of the reaction chamber setting part 511, two holding holes 511a each having an open top are formed. Into the two holding holes 511a, a reaction chamber M for mixing a reagent and a sample is set.

Figure 4:
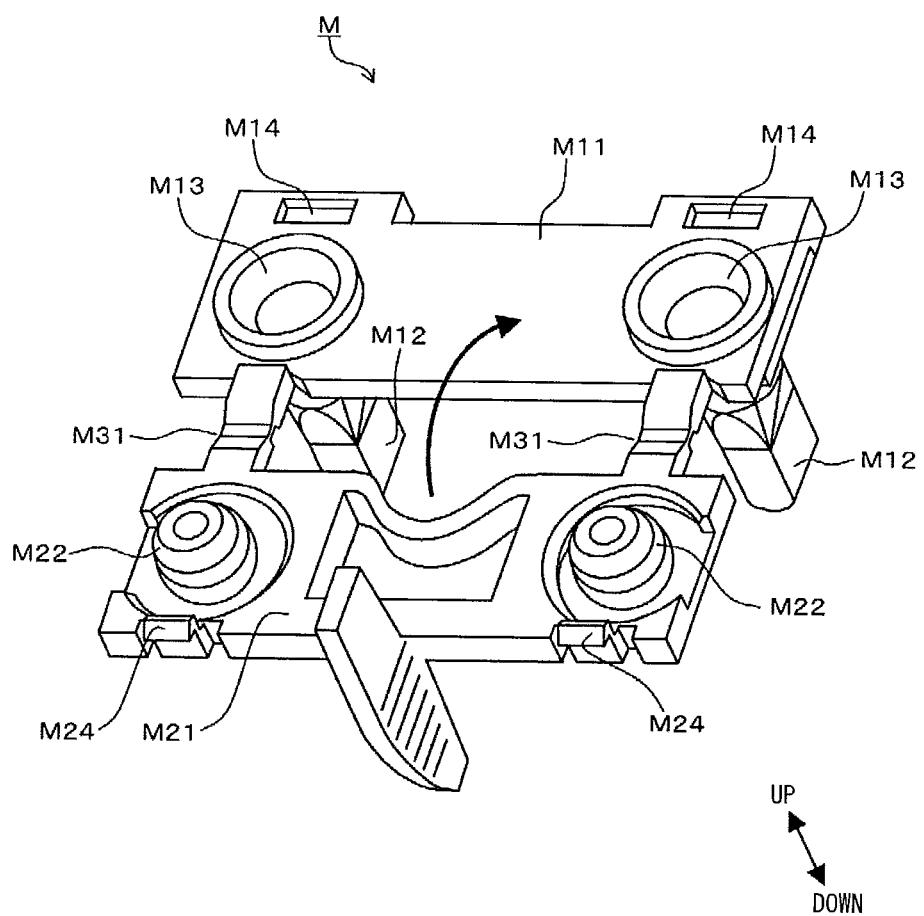
FIG. 4 is a perspective view showing a structure of a reaction chamber.

FIG. 4 is a perspective view showing a structure of the reaction chamber M.

The reaction chamber M includes a chamber body part M11 and a cap part M21. The chamber body part M11 and the cap part M21 are rotatably connected to each other by means of two connection parts M31. In the chamber body part M11, two receptacles M12 each extending in the up-down direction are formed. The upper part of each receptacle M12 is upwardly open by means of an opening M13. In the chamber body part M11, two holes M14 penetrating the chamber body part M11 in the up-down direction are formed.

The cap part M21 is provided with two caps M22 each having a protruding shape and two claws M24. When the cap part M21 is folded back in the direction of the arc-like arrow in FIG. 4 with the connection parts M31 bended, and the two claws M24 are engaged with the holes M14, respectively, the left cap M22 is fitted into the left receptacle M12, whereby the left receptacle M12 is sealed, and the right cap M22 is fitted into the right receptacle M12, whereby the right receptacle M12 is sealed.

In a state where the openings M13 are open as shown in FIG. 4, the operator sets the reaction chamber M in a reaction chamber setting part 511. At this time, the reaction chamber M is set in the reaction chamber setting part 511 such that the right receptacle M12 and the left receptacle M12 shown in FIG. 4 are respectively held in the left holding hole 511a and the right holding hole 511a of the reaction chamber setting part 511 shown in FIG. 2.

Below the reaction chamber setting part 511, light-emitters and light-receivers are provided. Light from each light-emitter passes through a receptacle M12 to be received by a corresponding light-receiver. In this manner, optical measurement of a sample is performed.

Figure 5:
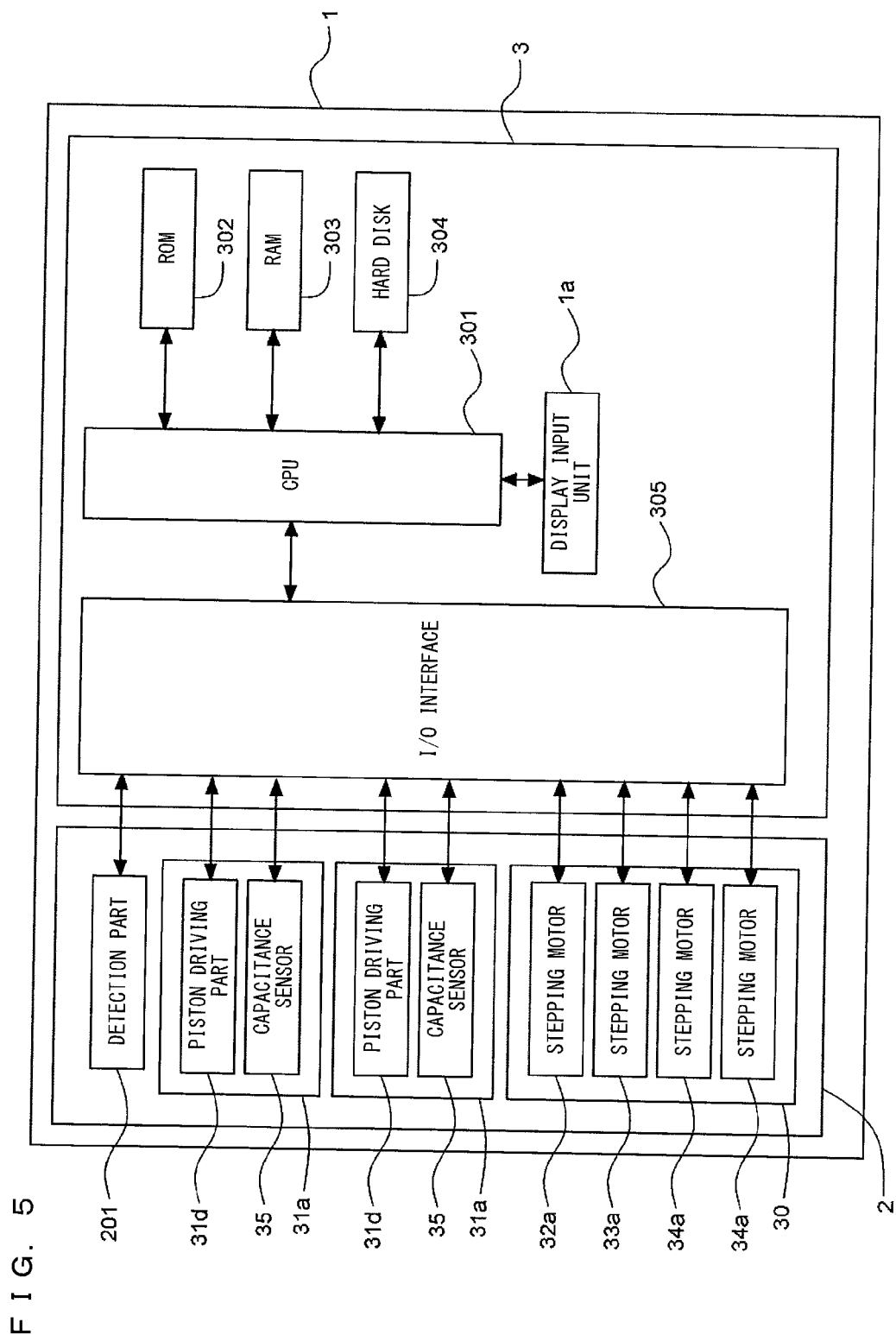
FIG. 5 is a block diagram showing a configuration of the sample processing apparatus according to the embodiment.

FIG. 5 is a block diagram showing a configuration of the sample processing apparatus 1.

The sample processing apparatus 1 includes a measurement unit 2 and an information process unit 3.

The measurement unit 2 includes the dispensing parts 31a shown in FIG. 3, a detection part 201, and the movement mechanism 30. The detection part 201 includes the light-emitters and the light-receivers described above. Each dispensing part 31a includes the piston driving part 31d and the capacitance sensor 35. The movement mechanism 30 includes: the stepping motor 32a for rotating the shaft 32 to move the arm part 31 in the X-axis direction; a stepping motor 33a for rotating the shaft 33 to move the arm part 31 in the Y-axis direction; and the stepping motor 34a for moving the dispensing part 31a in the Z-axis direction.

The information process unit 3 includes a CPU 301, a ROM 302, a RAM 303, a hard disk 304, an I/O interface 305, and the display input unit 1a shown in FIG. 1.

The CPU 301 executes computer programs stored in the ROM 302 and computer programs loaded onto the RAM 303. The RAM 303 is used for reading out computer programs stored in the ROM 302 and the hard disk 304. The RAM 303 is also used as a work area for the CPU 301 when the CPU 301 executes these computer programs.

The hard disk 304 has stored therein various computer programs to be executed by the CPU 301, such as an operating system and application programs, and data to be used in execution of the computer programs.

The display input unit 1a is a display of a touch panel type. The display input unit 1a receives inputs from the operator and displays an image, thereby presenting information to the operator. The I/O interface 305 is connected to the CPU 301, the display input unit 1a, and components of the measurement unit 2. The CPU 301 receives signals from these mechanisms connected to the I/O interface 305, and controls these mechanisms.

Next, with reference to FIG. 2, sample measuring operation will be described.

When performing sample measurement, the operator registers a measurement order via the display input unit 1a. Then, the operator prepares a sample by performing pre-treatment such as homogenization, centrifugation, dilution, and the like onto an excised tissue to be measured.

Subsequently, the operator opens the cover 1b. The operator sets a sample container containing the prepared sample and a sample container containing a diluted sample obtained by diluting this sample, into predetermined holding holes 11 of the sample container setting part 10. The operator sets a reagent container containing the CK19 primer reagent and a reagent container containing the β actin primer reagent, into the holding holes 21. The operator sets a reagent container containing the enzyme reagent in the holding hole 22. The operator sets a reaction chamber M into a predetermined reaction chamber setting part 511 of the reaction part 50. Then, the operator closes the cover 1b to start measurement. CK19 is a protein that is usually present in epithelial cells and not present in lymph nodes. However, when a cancer has metastasized, CK19 appears in lymph nodes. By amplifying cDNA from a template mRNA of CK19, cancer-derived nucleic acid present in the excised tissue can be detected. β actin is a protein expressed in various tissues. By amplifying cDNA from a template mRNA of β actin, whether nucleic acid amplification is being normally conducted can be confirmed.

Upon start of measurement, the arm part 31 is moved by the movement mechanism 30 from an origin position (a position at a right front portion inside the sample processing apparatus 1) to above the tip setting part 40. The two dispensing parts 31a are located above pipette tips C, respectively.

Figure 6:
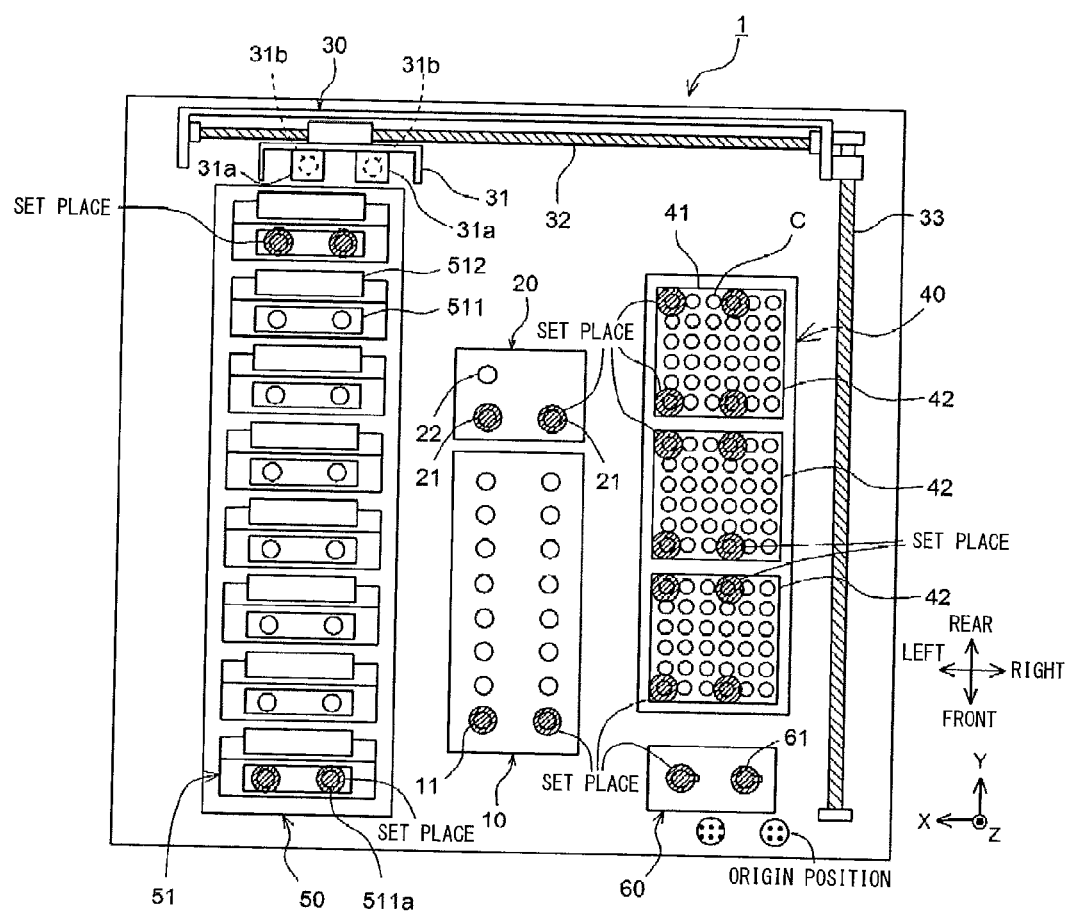
FIG. 6 is a plan view of the inside of the sample processing apparatus, schematically showing set places at each of which reference position information is set.

Now, positioning of the dispensing parts 31a will be described. For positioning of the dispensing parts 31a, reference position information stored in the hard disk 304 is used. As reference position information, a reference position is set for each of a plurality of places inside the sample processing apparatus 1. FIG. 6 is a plan view of the inside of the sample processing apparatus 1, schematically showing set places at each of which reference position information is set. In FIG. 6, circles shaded with diagonal lines represent set places of reference position information. A pair of circles arranged side by side in the left-right direction indicate positions of a pair of dispensing parts 31a arranged side by side in the left-right direction. The pair of positions indicated by the two circles arranged side by side in the left-right direction form one group, whereby one set place is defined. As shown in FIG. 6, there are 11 set places of reference position information in total, i.e., 6 places in the tip setting part 40, 1 place in the tip disposal part 60, 1 place in the sample container setting part 10, 1 place in the reagent container setting part 20, and 2 places in the reaction part 50.

In positioning the dispensing parts 31a, reference position information of the set place of the portion (any of the sample container setting part 10, the reagent container setting part 20, the tip setting part 40, the reaction part 50, and the tip disposal part 60) being the movement destination of the dispensing parts 31a is used. For example, in a case where the dispensing parts 31a are positioned in the tip setting part 40 as above, reference position information corresponding to a rack set part 42 of the movement destination is used. Since two set places are provided in one rack set part 42, either one (or both) of the two pieces of reference position information is to be used.

Reference position information is information indicating the reference position of each set place. Specifically, the reference position information is the number of pulses of the stepping motor 32a and the number of pulses of the stepping motor 33a for moving the dispensing parts 31a from the origin position to the reference position. In positioning the dispensing parts 31a, reference position information of a set place corresponding to the portion of movement destination is read out from the hard disk 304. Based on this reference position information and relative position information from the reference position to the target position, the numbers of pulses of the stepping motors 32a and 33a are obtained. The stepping motor 32a and 33a are driven by these numbers of pulses, whereby the dispensing parts 31a are positioned at the target position.

When the dispensing parts 31a are located above the tip setting part 40, the dispensing parts 31a are moved downward, and pipette tips C are attached to the nozzle parts 31b, respectively.

When the pipette tips C are attached to the respective dispensing parts 31a, the arm part 31 is moved to above the reagent container setting part 20 by the movement mechanism 30. At this time, reference position information corresponding to one set place of the reagent container setting part 20 is read out from the hard disk 304. Then, positioning of the dispensing parts 31a is performed.

With regard to aspiration of a reagent, depending on measurement items, there are a case where the CK19 primer reagent is aspirated into both of the two dispensing parts 31a, and a case where the CK19 primer reagent is aspirated into one dispensing part 31a and the β actin primer reagent is aspirated into the other dispensing part 31a.

In a case where the CK19 primer reagent is aspirated into both of the two dispensing parts 31a, one dispensing part 31a is located above the CK19 primer reagent container. Then, this dispensing part 31a is moved downward, the leading end of one pipette tip C is inserted into the CK19 primer reagent container, and the CK19 primer reagent is aspirated from the reagent container. At this time, the liquid surface is detected by the capacitance sensor 35. The dispensing part 31a is lowered by a predetermined distance from the height at which the liquid surface has been detected, and then, the reagent is aspirated. After this dispensing part 31*a* is raised and the pipette tip C is separated from the reagent container, the other dispensing part 31*a* is located above the CK19 primer reagent container. From this state, this dispensing part 31*a* is moved downward, and the leading end of the other pipette tip C is inserted into the CK19 primer reagent container. Then, as in the case of the one dispensing part 31*a*, the CK19 primer reagent is aspirated from the reagent container. In this manner, the CK19 primer reagent is held in the two pipette tips C.

In a case where the CK19 primer reagent is aspirated into one dispensing part 31*a* and the β actin primer reagent is aspirated into the other dispensing part 31*a*, one dispensing part 31*a* is located above the CK19 primer reagent container and the other dispensing part 31*a* is located above the β actin primer reagent container. From this state, the two dispensing parts 31*a* are moved downward, and the leading end of one pipette tip C is inserted into the CK19 primer reagent container, and the leading end of the other pipette tip C is inserted into the β actin primer reagent container. Then, the CK19 primer reagent and the β actin primer reagent are respectively aspirated from the reagent containers at the same time by the two dispensing parts 31*a*. In this manner, the CK19 primer reagent and the β actin primer reagent are held in the two pipette tips C, respectively.

When the CK19 primer reagent (or the β actin primer reagent) is aspirated in each dispensing part 31*a*, the arm part 31 is moved to above the reaction part 50 by the movement mechanism 30, and the two dispensing parts 31*a* are located above the two openings M13 of one reaction chamber M. At this time, either of the two pieces of the reference position information corresponding to the two set places of the reaction part 50 is read out from the hard disk 304, and positioning of the dispensing parts 31*a* is performed.

When the dispensing parts 31*a* are located above the reaction part 50, the dispensing parts 31*a* are moved downward, the leading ends of the pipette tips C are inserted into the two receptacles M12 of the reaction chamber M, and the CK19 primer reagent (or the β actin primer reagent) is discharged into the receptacles M12. Then, the dispensing parts 31*a* are moved upward. Depending on the case, the reagent is not dispensed into the two receptacles M12 of the same reaction chamber M, but instead, the reagent is dispensed into receptacles M12 of two reaction chambers M.

Upon completion of discharge of the primer reagent, the arm part 31 is moved to above the tip disposal part 60 by the movement mechanism 30, and the dispensing parts 31*a* are located above the two disposal holes 61, respectively. At this time, reference position information corresponding to the set place of the tip disposal part 60 is read out from the hard disk 304, and positioning of the dispensing parts 31*a* is performed.

When the dispensing parts 31*a* are positioned above the tip disposal part 60, these dispensing parts 31*a* are moved downward, the two pipette tips C are inserted into the disposal holes 61, respectively, and further, the arm part 31 is moved in the right direction. Thus, the nozzle parts 31*b* are located at the cutouts 61*a*, respectively. Then, the dispensing parts 31*a* are moved upward, whereby the pipette tips C are discarded.

By repeating the attachment of the pipette tips, the aspiration of the primer reagent, the discharge of the primer reagent, and the discarding of the pipette tips described above, the primer reagent is dispensed into all the reaction chambers M.

Upon completion of dispensing of the primer reagent, the arm part 31 is moved to above the tip setting part 40 by the movement mechanism 30, and in the same manner as above, new pipette tips C are attached to the respective dispensing parts 31*a*.

After the pipette tips C have been attached to the respective dispensing parts 31*a*, the arm part 31 is moved to above the reagent container setting part 20 by the movement mechanism 30. Then, one dispensing part 31*a* is located above the enzyme reagent container. From this state, this dispensing part 31*a* is moved downward, and the leading end of one pipette tip C is inserted into the enzyme reagent container. The liquid surface of the enzyme reagent is detected, and then, the enzyme reagent is aspirated from the reagent container. After this dispensing part 31*a* is raised and the pipette tip C is separated from the reagent container, the other dispensing part 31*a* is located above the enzyme reagent container. From this state, this dispensing part 31*a* is moved downward, and the leading end of the other pipette tip C is inserted into the enzyme reagent container. After the liquid surface of the enzyme reagent is detected, the enzyme reagent is aspirated from the reagent container. In this manner, the enzyme reagent is held in the two pipette tips C.

After the enzyme reagent has been aspirated in each dispensing part 31*a*, the arm part 31 is moved to above the reaction part 50 by the movement mechanism 30, and the dispensing parts 31*a* are located above the two openings M13 of one reaction chamber M. From this state, the dispensing parts 31*a* are moved downward, and the leading ends of the pipette tips C are respectively inserted into the two receptacles M12 of the reaction chamber M. Then, the enzyme reagent is discharged into the receptacles M12. Then, the dispensing parts 31*a* are moved upward.

Upon completion of discharge of the enzyme reagent, in each receptacle M12 of the reaction chamber M, the primer reagent and the enzyme reagent are agitated. Then, the arm part 31 is moved to above the tip disposal part 60 by the movement mechanism 30. In the same manner as above, the pipette tips C attached to the dispensing parts 31*a* are discarded.

By repeating the attachment of the pipette tips, the aspiration of the enzyme reagent, the discharge of the enzyme reagent, and the discarding of the pipette tips described above, the enzyme reagent is dispensed into all the reaction chambers M.

Upon completion of dispensing of the enzyme reagent, the arm part 31 is moved to above the tip setting part 40 by the movement mechanism 30, and in the same manner as above, new pipette tips C are attached to the respective dispensing parts 31*a*.

After the pipette tips C have been attached to the respective dispensing parts 31*a*, the arm part 31 is moved to above the sample container setting part 10 by the movement mechanism 30. Then, the dispensing parts 31*a* are located above two sample containers arranged side by side in the left-right direction, respectively. At this time, reference position information corresponding to one set place of the sample container setting part 10 is read out from the hard disk 304, and positioning of the dispensing parts 31*a* is performed.

After the dispensing parts 31*a* have been located above the sample container setting part 10, the dispensing parts 31*a* are moved downward, and the leading ends of the pipette tips C are respectively inserted into the two sample containers. The liquid surfaces of the sample and the diluted sample are detected, and then, the sample and the diluted sample are aspirated from the sample containers, respectively. Thereafter, the dispensing parts 31*a* are raised and the pipette tips C are separated from the sample containers.

After the sample and the diluted sample have been aspirated in the respective dispensing part 31a, the arm part 31 is moved to above the reaction part 50 by the movement mechanism 30, and the dispensing parts 31a are located above the two openings M13 of one reaction chamber M, in the same manner as above. From this state, the dispensing parts 31a are moved downward, and the leading ends of the pipette tips C are respectively inserted into the two receptacles M12 of the reaction chamber M. The sample is discharged into one receptacle M12, and the diluted sample is discharged into the other receptacle M12. Then, the dispensing parts 31a are moved upward. Depending on the case, the sample and the diluted sample are not respectively dispensed into the two receptacles M12 of the same reaction chamber M, but instead, the sample and the diluted sample are respectively dispensed into receptacles M12 of two reaction chambers M.

Upon completion of discharge of the sample and the diluted sample, in each receptacle M12 of the reaction chamber M, the sample (diluted sample) and the reagent are agitated. Then, the arm part 31 is moved to above the tip disposal part 60 by the movement mechanism 30. In the same manner as above, the pipette tips C attached to the dispensing parts 31a are discarded.

By repeating the attachment of the pipette tips, the aspiration of the sample and the diluted sample, the discharge of the sample and the diluted sample, and the discarding of the pipette tips described above, the sample and the diluted sample are dispensed into all the reaction chambers M.

Next, with respect to each reaction chamber M, the cap part M21 is folded back in the direction of the arrow in FIG. 4 in the reaction part 50, and the two receptacles M12 are sealed with the caps M22, respectively. In this state, the temperature in the reaction chamber M is heated to about 20 to 65° C. by a Peltier module (not shown) provided below the reaction chamber setting part 511, and the nucleic acid is amplified through LAMP reaction. Then, as described above, light emitted from the light-emitter passes through each receptacle M12 of the reaction chamber M and is received by the light-receiver. At this time, based on the signal detected by the light-receiver, turbidity inside the receptacle M12 during nucleic acid amplification reaction is obtained in real time. Based on the obtained turbidity and a calibration curve created in advance from a result of measurement of the calibrator, the concentration of the target nucleic acid is obtained from the amplification rise time. Then, the sample measurement ends.

As described above, in the sample processing apparatus 1, during sample measuring operation, the dispensing parts 31a are moved by the movement mechanism, to a rack 41 in the tip setting part 40, sample containers in the sample container setting part 10, reagent containers in the reagent container setting part, reaction chambers in the reaction part, and the tip disposal part. Thus, the dispensing parts 31a are positioned in horizontal directions. If such positioning of the dispensing parts 31a is not accurately performed, pipette tips C cannot be properly attached to the dispensing parts 31a, the sample or the reagent cannot be normally aspirated from the sample container or the reagent container, the sample or the reagent cannot be normally discharged into the reaction chamber, and pipette tips C cannot be properly discarded. Therefore, in an adjustment step at a plant after production of the sample processing apparatus 1 according to the present embodiment, the following automatic position adjustment process is performed. The automatic position adjustment process may be performed not only in the adjustment step at a plant, but also performed in maintenance operation by a service person after the sample processing apparatus 1 has been set in a medical institution (hospital, test center, or the like) or in adjustment operation after repair of the sample processing apparatus 1 that has failed.

<Automatic Position Adjustment Process>

In the automatic position adjustment process, at a plurality of set places (see FIG. 6) inside the sample processing apparatus 1 described above, position adjustment of the dispensing parts 31a is performed. At each set place, position adjustment of the two dispensing parts 31a arranged side by side in the left-right direction is performed simultaneously.

With respect to the tip setting part 40, in each of the three rack set parts 42, two set places are provided at the front side and the rear side. For the tip disposal part 60, the disposal holes 61 serve as a set place. For the sample container setting part 10, the two holding holes 11 at the front end serve as a set place. For the reagent container setting part 20, the holding holes 21 which hold the CK19 primer reagent container and the β actin primer reagent container serve as a set place. For the reaction part 50, two holding holes 511a of the reaction detection block 51 at the front end, and two holding holes 511a of the reaction detection block 51 at the rear end serve as set places.

Figure 7A:
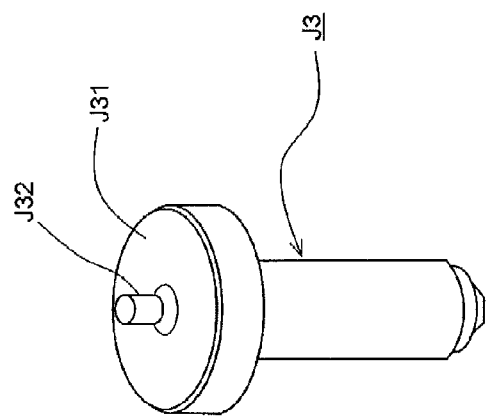
FIG. 7A is a perspective view showing a position adjustment jig for a tip setting part.
Figure 7C:
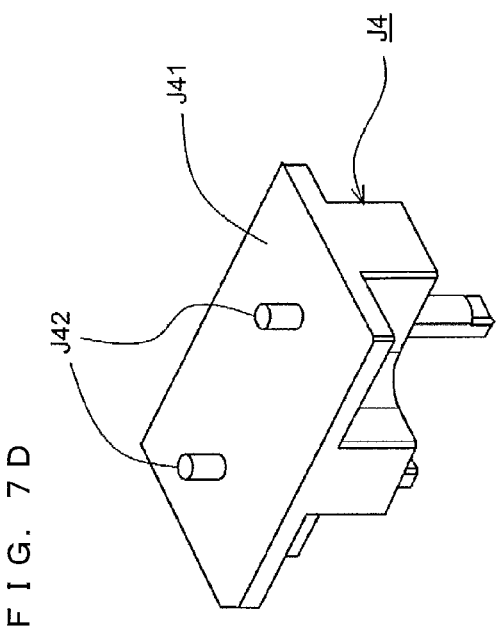
FIG. 7C is a perspective view showing a position adjustment jig for a sample container setting part and a reagent container setting part.
Figure 7B:
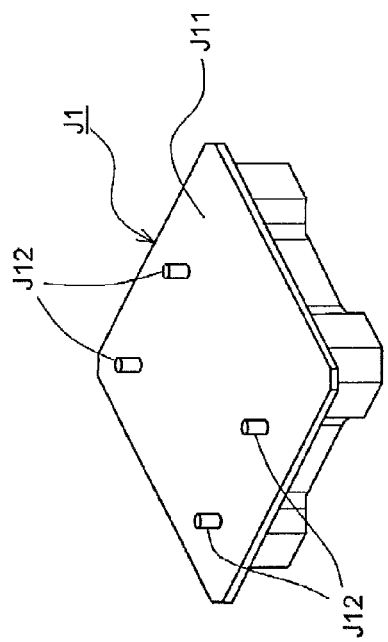
FIG. 7B is a perspective view showing a position adjustment jig for a tip disposal part.
Figure 7D:
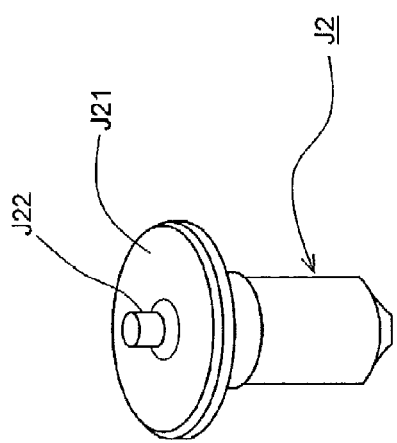
FIG. 7D is a perspective view showing a position adjustment jig for a reaction part.

In the automatic position adjustment process, position adjustment jigs made of a conductive material such as carbon steel is used. FIG. 7A to FIG. 7D are perspective views showing the position adjustment jigs. FIG. 7A shows a position adjustment jig for the tip setting part 40. FIG. 7B shows a position adjustment jig for the tip disposal part 60. FIG. 7C shows a position adjustment jig for the sample container setting part 10 and the reagent container setting part 20. FIG. 7D shows a position adjustment jig for the reaction part 50. As shown in FIG. 7A to FIG. 7D, a position adjustment jig J1 for the tip setting part 40 has a shape that can be inserted into a rack set part 42. A position adjustment jig J2 for the tip disposal part 60 has a shape that can be inserted into a disposal hole 61. A position adjustment jig J3 for the sample container setting part 10 and the reagent container setting part 20 has a shape that can be inserted into a holding hole 11 and a holding hole 21. A position adjustment jig J4 for the reaction part 50 has a shape that can be inserted into a reaction chamber setting part 511. The top faces of the position adjustment jigs J1 to J4 are flat surfaces J11 to J41, respectively. From the respective flat surfaces J11 to J41, protrusions J12 to J42 each having a cylindrical shape that protrudes upward are provided. Each of the protrusions J12 to J42 has an upper end face which is flat. Each of the protrusions J12 to J42 has the same area and the same shape. The outer shape of the upper end face of each of the protrusions J12 to J42 is a circle having the same diameter as that of the lower end face of the nozzle part 31b.

As preparation for the automatic position adjustment process, an operator attaches the position adjustment jigs J1 to J4 described above to the sample processing apparatus 1. At this time, for the tip setting part 40, the operator mounts three position adjustment jigs J1 on the respective rack set parts 42. For the tip disposal part 60, the operator mounts two position adjustment jigs J2 on the respective disposal holes 61. For the sample container setting part 10, the operator mounts two position adjustment jigs J3 on the two holding holes 11 at the front end. For the reagent container setting part 20, the operator mounts two position adjustment jigs J3 on the two holding holes 21. For the reaction part 50, the operator mounts two position adjustment jigs J4 on each of the reaction chamber setting part 511 at the front end and the reaction chamber setting part 511 at the rear end. In the present embodiment, the automatic position adjustment process is performed without pipette tips C being attached to the dispensing parts 31a. However, since each pipette tip C is electrically conductive and functions as an electrode of the capacitance sensor 35, the automatic position adjustment process may be performed by use of the dispensing parts 31a having pipette tips C attached thereto.

Upon completion of the mounting of the position adjustment jigs J1 to J4, the operator operates the display input unit 1a to instruct start of the automatic position adjustment process. Upon receiving the instruction to start the automatic position adjustment process, the CPU 301 executes the automatic position adjustment process described below.

Figure 8:
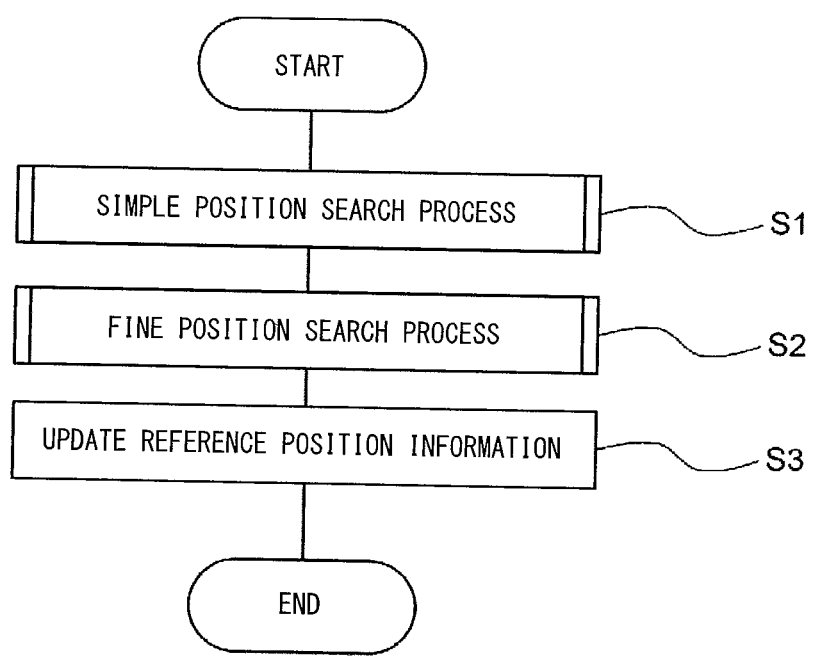
FIG. 8 is a flow chart showing the procedure of an automatic position adjustment process.

FIG. 8 is a flow chart showing the procedure of the automatic position adjustment process.

Upon starting the automatic position adjustment process, first, the CPU 301 executes a simple position search process for roughly searching the position of each of the protrusions J12 to J42 (step S1). Then, the CPU 301 executes a fine position search process for finely searching the position of each of the protrusions J12 to J42 (step S2). In this manner, in the present embodiment, the position of each of the protrusions J12 to J42 is searched in two stages. In the simple position search process and the fine position search process, when searching the position of each of the protrusions J12 to J42, the capacitance sensor 35 is used.

FIG. 9 is a schematic diagram for explaining the outline of search of the positions of the protrusions J12 to J42. The simple position search process is a process in which, at each set place, the movement mechanism 30 is controlled such that the dispensing parts 31a are moved in a simple search region SA1 being a large search range which covers a dimensional variation range, and the simple search region SA1 is scanned by the capacitance sensor 35. The simple search region SA1 is a range of dimensional variation due to dimensional tolerance and assembling accuracy of parts of the sample processing apparatus 1 and mounting accuracy of the position adjustment jigs J1 to J4 plus a surplus. The simple search region SA1 is set so as to include therein the position of the protrusion J12 to J42. Through the simple position search process, the position of the protrusion J12 to J42 of the position adjustment jig J1 to J4 is roughly searched. In the simple position search process, the height of the protrusion J12 to J42 is also detected.

On the other hand, the fine position search process is a process in which, at each set place, a fine search region SA2 being a small search range including the position (hereinafter, referred to as "rough position") of the protrusion J12 to J42 searched in the simple position search process is set, the movement mechanism 30 is controlled such that the dispensing parts 31a are moved in the fine search region SA2, and the fine search region SA2 is scanned by the capacitance sensor 35. Through the fine position search process, the position of the protrusion J12 to J42 of the position adjustment jig J1 to J4 is finely searched. The position searched in the fine position search process is determined as the position of the protrusion J12 to J42 of the position adjustment jig J1 to J4.

When the fine position search process ends, the CPU 301 stores, in the hard disk 304, pieces of position information respectively indicating the positions of the protrusions J12 to J42 of the position adjustment jigs J1 to J4 searched as above. Then, the CPU 301 updates each pieces of reference position information (step S3). The position information indicating the position of the protrusion J12 to J42 is the number of pulses of the stepping motors 32a and 33a for moving the dispensing parts 31a from the origin position to the position of the protrusion J12 to J42, and the number of pulses of the stepping motor 34a for lowering the dispensing parts 31a from a predetermined reference height.

When the reference position information is updated as above, the CPU 301 ends the automatic position adjustment process.

Figure 10:
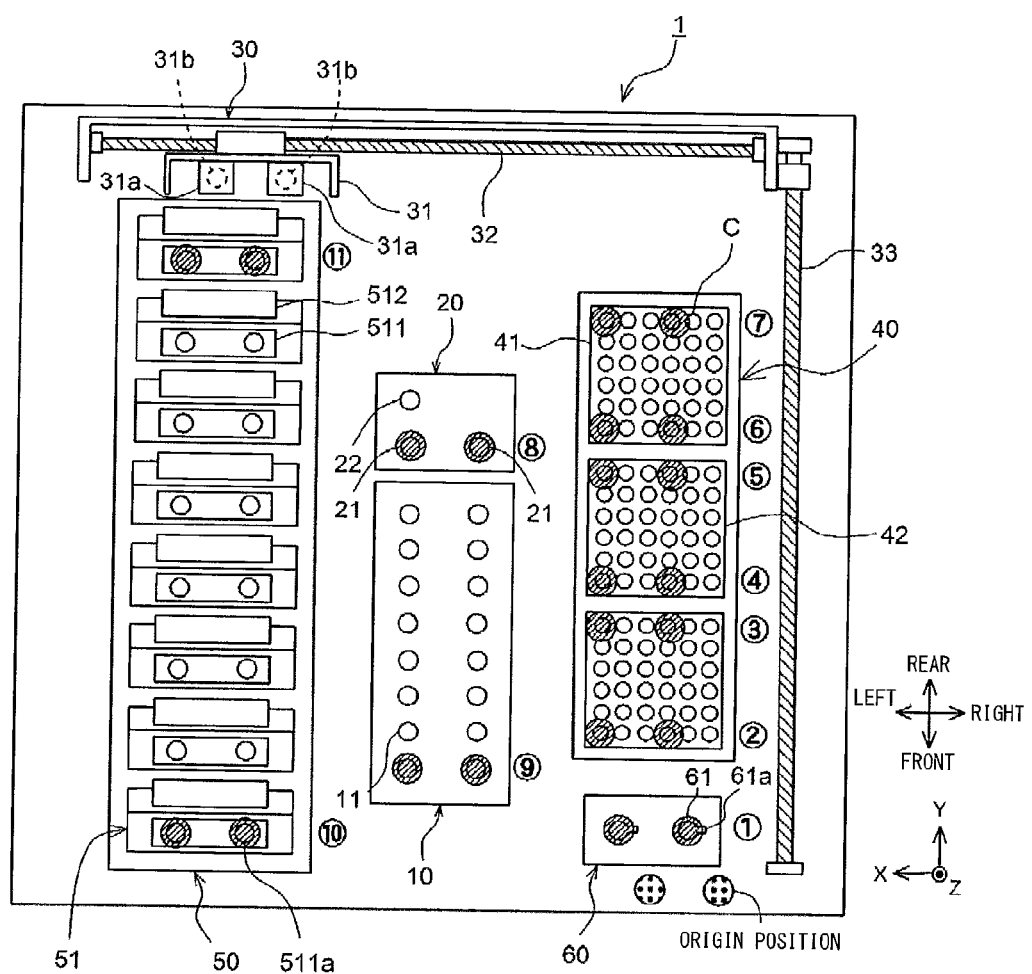
FIG. 10 is a plan view of the inside of the sample processing apparatus for explaining the order of position adjustment in a simple position search process.

Next, the simple position search process will be described in detail. In the simple position search process, the positions of the protrusions J12 to J42 are searched in order at the set places described above. FIG. 10 is a plan view of the inside of the sample processing apparatus 1 for explaining the order of position adjustment in the simple position search process. As shown in FIG. 10, in the simple position search process, first, the search place of the tip disposal part 60 is searched. Then, the set place on the front-most side of the tip setting part 40 to the set place on the rear-most side are searched in order. Then, the set place of the reagent container setting part 20 is searched. Then, the set place of the sample container setting part 10 is searched. Then, the search place on the front side and the search place on the rear side of the reaction part 50 are searched in order. The circled numbers in FIG. 10 show the order of the search.

Figure 11A:
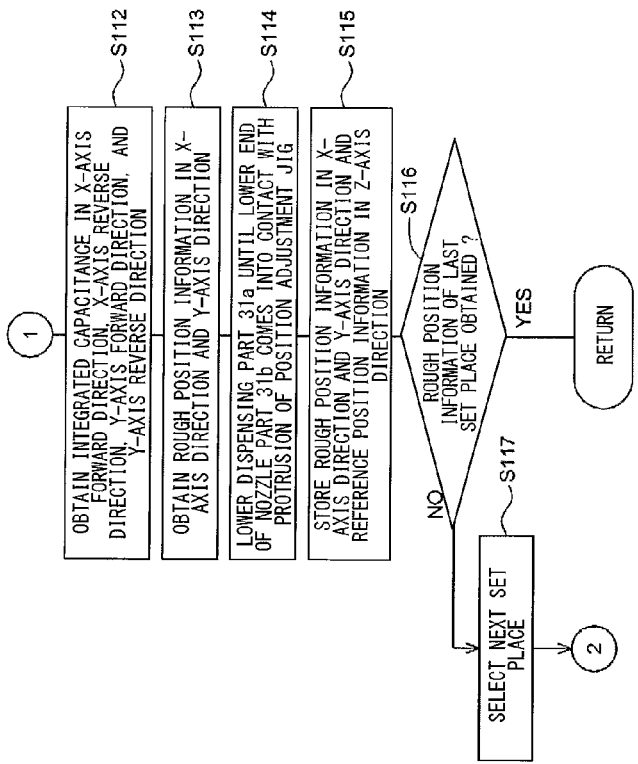
FIG. 11A is a flow chart (first half) showing the procedure of the simple position search process.
Figure 11B:
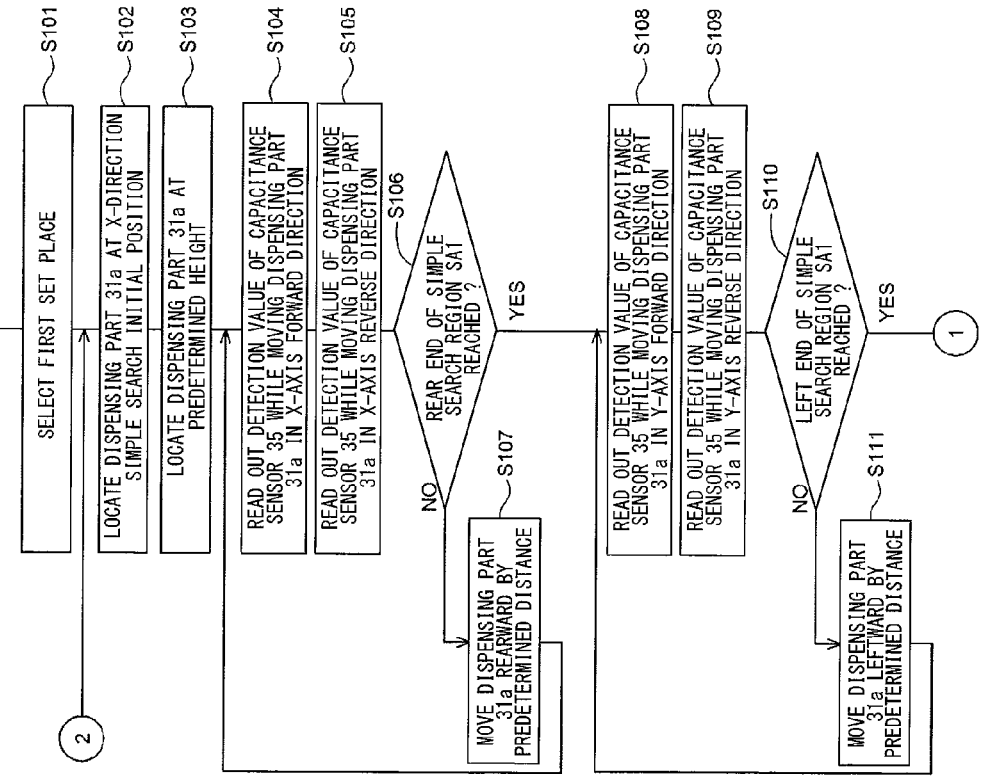
FIG. 11B is the flow chart (second half) showing the procedure of the simple position search process.

FIG. 11A and FIG. 11B are a flow chart showing the procedure of the simple position search process. In the simple position search process, first, the CPU 301 selects the first set place (i.e., the set place of the tip disposal part 60) (step S101). Next, the CPU 301 controls the stepping motors 32a and 33a to locate the two dispensing parts 31a at an X-direction simple search initial position of the selected search place (step S102).

Figure 12A:
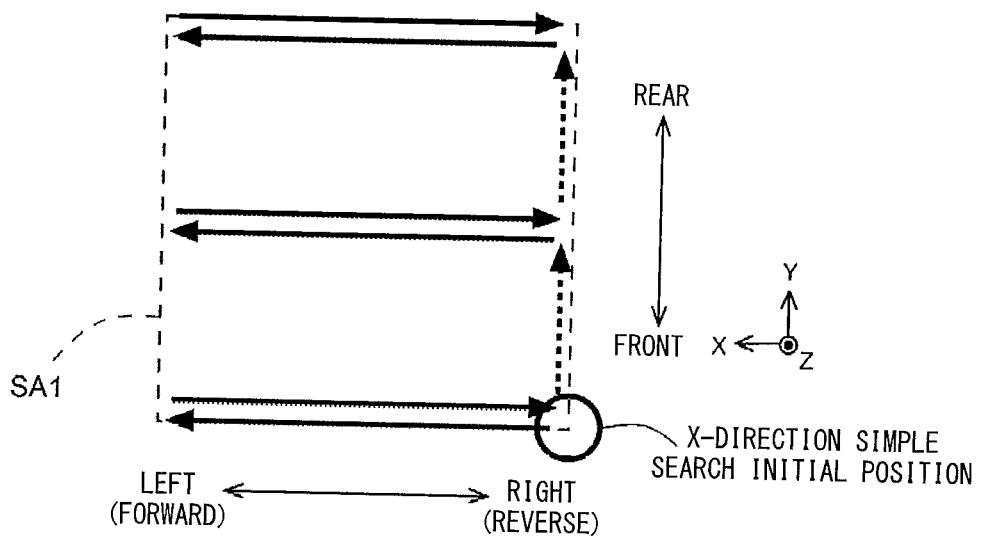
FIG. 12A is a schematic diagram for explaining the simple position search in an X-axis direction.

FIG. 12A is a schematic diagram for explaining the simple position search in the X-axis direction. As shown in FIG. 12A, the X-direction simple search initial position is the position at the right front corner of the simple search region SA1. After the dispensing parts 31a are located at this position, the CPU 301 controls the stepping motor 34a to locate the dispensing parts 31a at a predetermined height (step S103). This height is set to a height that allows the lower end of each nozzle part 31b to be located about 3 to 5 mm above the upper end of the protrusion J12 to J42, with a surplus to the dimensional variation of the product.

Next, the CPU 301 controls the stepping motor 32a to move the dispensing parts 31a leftward (hereinafter, referred to as "X-axis forward direction") at a predetermined speed (hereinafter, referred to as "simple search speed"). Then, the CPU 301 reads out detection values of the capacitance sensor 35 at a predetermined sampling interval (hereinafter, referred to as "simple search sampling interval") during this time. Then, the CPU 301 stores the detection values in an internal memory of the CPU 301 (step S104). Thus, at each predetermined distance (hereinafter, referred to as "simple search sampling distance") in the X-axis direction determined by the simple search speed and the simple search sampling interval, the detection value of the capacitance sensor 35 is intermittently read out.

When the above scan has reached the left end of the simple search region SA1, the CPU 301 controls the stepping motor 32a to move the dispensing parts 31a rightward (hereinafter, referred to as "X-axis reverse direction") at the simple search speed. Then, the CPU 301 reads out detection values of the capacitance sensor 35 at the simple search sampling interval during this time. Then, the CPU 301 stores the detection values in the internal, memory of the CPU 301 (step S105). Thus, at each simple search sampling distance in the X-axis direction, the detection value of the capacitance sensor 35 is intermittently read out.

When the above scan has reached the right end of the simple search region SA1, the CPU 301 determines whether the search has been completed up to the rear end of the simple search region SA1 (step S106). When the search has not been completed up to the rear end of the simple search region SA1 (NO in step S106), the CPU 301 controls the stepping motor 33a to move the dispensing parts 31a rearward by a predetermined distance (step S107). Detection values of the capacitance sensor 35 during this movement rearward are not read out.

When the dispensing parts 31a have been moved rearward by the predetermined distance, the CPU 301 returns the process to step S104, to execute the process of step S104 (simple scan in the X-axis forward direction) and the process of S105 (simple scan in the X-axis reverse direction) again.

In step S106, when the search has been completed up to the rear end of the simple search region SA1 (YES in step S106), the CPU 301 shifts the process to step S108. In the present embodiment, the numbers of times of the simple scan in the X-axis forward direction and the X-axis reverse direction are three, respectively. However, the numbers of times of the simple scan in the X-axis forward direction and the X-axis reverse direction are not limited thereto.

Figure 12B:
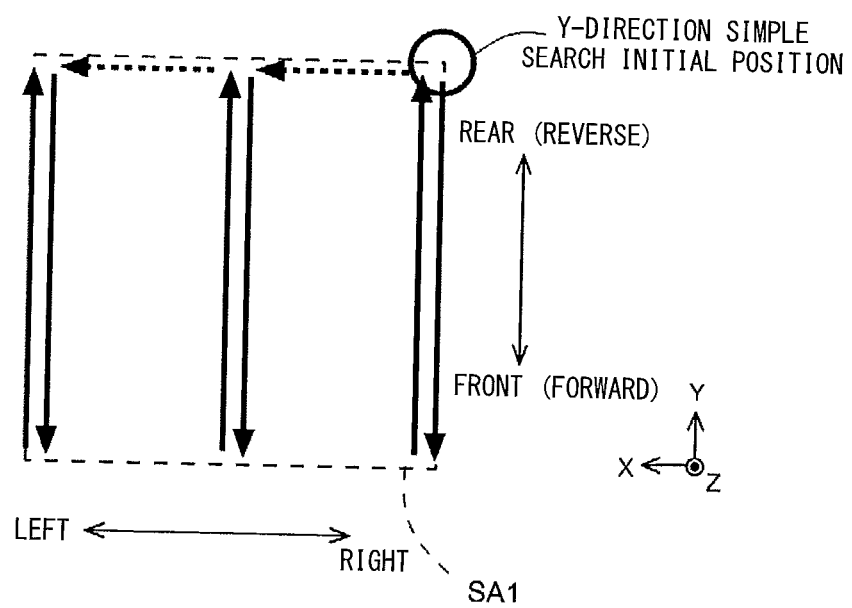
FIG. 12B is a schematic diagram for explaining the simple position search in a Y-axis direction.

FIG. 12B is a schematic diagram for explaining the simple position search in the Y-axis direction. When the last simple search in the X-axis reverse direction has been completed, the dispensing parts 31a are located at the right rear corner (hereinafter, referred to as "Y-direction simple search initial position") of the simple search region SA1. In a state where the dispensing parts 31a are located at this position, the CPU 301 controls the stepping motor 33a to move the dispensing parts 31a forward (hereinafter, referred to as "Y-axis forward direction") at the simple search speed. Then, the CPU 301 reads out detection values of the capacitance sensor 35 at the simple search sampling interval during this time. Then, the CPU 301 stores the detection values in the internal memory of the CPU 301 (step S108). Thus, at each simple search sampling distance in the Y-axis direction, the detection value of the capacitance sensor 35 is intermittently read out.

When the above scan has reached the front end of the simple search region SA1, the CPU 301 controls the stepping motor 33a to move the dispensing parts 31a rearward (hereinafter, referred to as "Y-axis reverse direction") at the simple search speed. Then, the CPU 301 reads out detection values of the capacitance sensor 35 at the simple search sampling interval during this time. Then, the CPU 301 stores the detection values in the internal memory of the CPU 301 (step S109). Thus, at each simple search sampling distance in the Y-axis direction, the detection value of the capacitance sensor 35 is intermittently read out.

When the above scan has reached the rear end of the simple search region SA1, the CPU 301 determines whether the search has been completed up to the left end of the simple search region SA1 (step S110). When the search has not been completed up to the left end of the simple search region SA1 (NO in step S110), the CPU 301 controls the stepping motor 32a to move the dispensing parts 31a leftward by a predetermined distance (step S111). Detection values of the capacitance sensor 35 during this movement leftward are not read out.

When the dispensing parts 31a have been moved leftward by the predetermined distance, the CPU 301 returns the process to step S108, to execute the process of step S108 (simple scan in the Y-axis forward direction) and the process of S109 (simple scan in the Y-axis reverse direction) again.

In step S110, when the search has been completed up to the left end of the simple search region SA1 (YES in step S110), the CPU 301 shifts the process to step S112. In the present embodiment, the numbers of times of the simple scan in the Y-axis forward direction and the Y-axis reverse direction are three, respectively. However, the numbers of times of the simple scan in the Y-axis forward direction and the Y-axis reverse direction are not limited thereto.

Figure 13A:
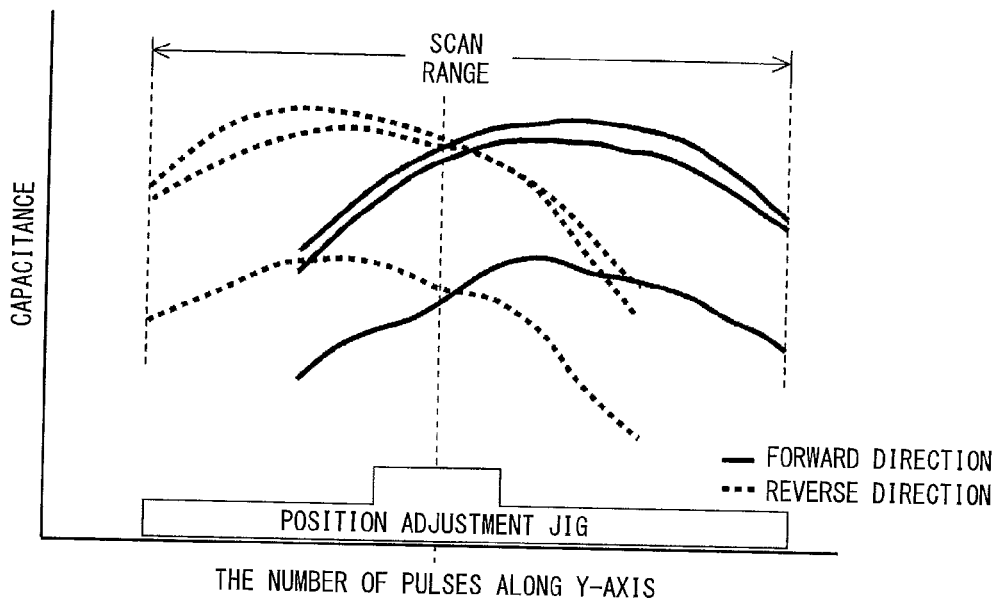
FIG. 13A is a graph showing relationship between position in the Y-axis direction and detection value of capacitance in a Y-axis forward direction and a Y-axis reverse direction.
Figure 13B:
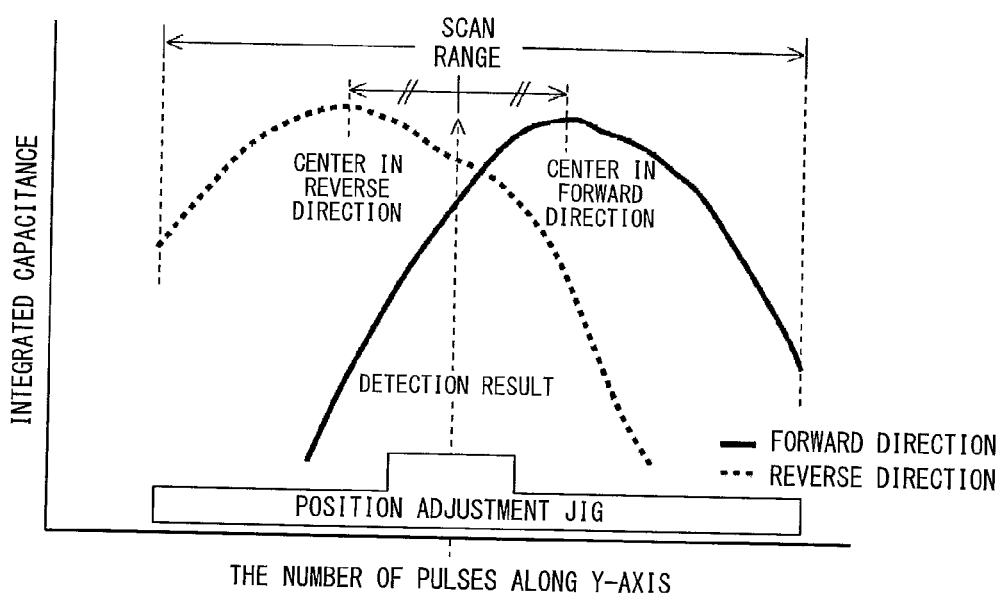
FIG. 13B is a graph showing relationship between position in the Y-axis direction and integrated capacitance in the Y-axis forward direction and the Y-axis reverse direction.

FIG. 13A is a graph showing relationship between position in the Y-axis direction and detection value of capacitance obtained through the scan in the Y-axis forward direction and the Y-axis reverse direction. FIG. 13B is a graph showing relationship between position in the Y-axis direction and integrated capacitance obtained by integrating, at each position in the Y-axis direction, detection values of capacitance obtained through the scan in the Y-axis forward direction, and relative to integrated capacitance obtained by integrating, at each position in the Y-axis direction, detection values of capacitance obtained through the scan in the Y-axis reverse direction.

Through three times of scan in each of the Y-axis forward direction and the Y-axis reverse direction, detection values of capacitance as indicated by the curves in FIG. 13A are obtained. In FIG. 13A, each curve of solid line indicates capacitance obtained through the scan in the Y-axis forward direction, and each curve of broken line indicates capacitance obtained through the scan in the Y-axis reverse direction. In a case where simple search is performed with regard to the position of a protrusion J12 of the position adjustment jig J1, the distance between the nozzle part 31b being the probe of the capacitance sensor 35 and the position adjustment jig J1 becomes shortest at the protrusion J12. Since the entirety of the position adjustment jig J1 is made of a conductive material, when a horizontal plane is assumed above the position adjustment jig J1, the magnitude of capacitance detected on the horizontal plane becomes greatest at the position immediately above the protrusion J12. In the present embodiment, since capacitance is detected while each nozzle part 31b is being moved in the horizontal direction, a lag occurs in the detection value of capacitance relative to movement of the nozzle part 31b. Thus, as shown in FIG. 13A, in the results of detection of capacitance in the Y-axis forward direction and the Y-axis reverse direction, peak positions differ from each other. That is, in the results of detection of capacitance in the Y-axis forward direction, the positions of the peaks are forward relative to the position of the protrusion J12. In the results of detection of capacitance in the Y-axis reverse direction, the positions of the peaks are rear relative to the position of the protrusion J12. It should be noted that the greater the protruding amount of the protrusion J12, the clearer peak appears in the detected capacitance, whereby more accurate measurement can be performed.

The CPU 301 integrates, for each position in the X-axis direction, detection values of capacitance obtained through the three times of scan in the X-axis forward direction, to obtain integrated capacitance in the X-axis forward direction. The CPU 301 integrates, for each position in the X-axis direction, detection values of capacitance obtained through the three times of scan in the X-axis reverse direction, to obtain integrated capacitance in the X-axis reverse direction. The CPU 301 integrates, for each position in the Y-axis direction, detection values of capacitance obtained through the three times of scan in the Y-axis forward direction, to obtain integrated capacitance in the Y-axis forward direction. The CPU 301 integrates, for each position in the Y-axis direction, detection values of capacitance obtained through the three times of scan in the Y-axis reverse direction, to obtain integrated capacitance in the Y-axis reverse direction. Then, the CPU 301 stores, in the internal memory of the CPU 301, the integrated capacitances in the X-axis forward direction, the X-axis reverse direction, the Y-axis forward direction, and the Y-axis reverse direction (step S112). For example, among the detection values of capacitance obtained through the three times of scan in the Y-axis forward direction shown in FIG. 13A, three detection values at the same position in the Y-axis direction are added together. By performing such addition of detection values for all detection positions in the Y-axis direction, the CPU 301 obtains integrated capacitance (see FIG. 13B) in the Y-axis forward direction. Among detection values of capacitance obtained through the three times of scan in the Y-axis reverse direction shown in FIG. 13A, three detection values at the same position in the Y-axis direction are added together. By performing such addition of detection values for all detection positions in the Y-axis direction, the CPU 301 obtains integrated capacitance (see FIG. 13B) in the Y-axis reverse direction. Similarly, also with respect to the X-axis forward direction and the X-axis reverse direction, integrated capacitance is obtained. In FIG. 13B, the curve of solid line indicates the integrated capacitance obtained through the scan in the Y-axis forward direction, and the curve of broken line indicates the integrated capacitance obtained through the scan in the Y-axis reverse direction.

Next, in step S113, the CPU 301 specifies the position in the X-axis direction of the peak of the integrated capacitance in the X-axis forward direction, and the position in the X-axis direction of the peak of the integrated capacitance in the X-axis reverse direction. Then, the CPU 301 determines the middle position (average value of coordinates in the X-axis direction) in the X-axis direction of both peaks. The CPU 301 obtains this middle position information as rough position information in the X-axis direction (the number of pulses of the stepping motor 32a for moving each dispensing part 31a from the origin position to the corresponding protrusion J12). Similarly, in step S113, the CPU 301 specifies the position in the Y-axis direction of the peak of the integrated capacitance in the Y-axis forward direction, and the position in the Y-axis direction of the peak of the integrated capacitance in the Y-axis reverse direction. Then, the CPU 301 determines the middle position (average value of coordinates in the Y-axis direction) in the Y-axis direction of both peaks. The CPU 301 obtains this middle position information as rough position information in the Y-axis direction (the number of pulses of the stepping motor 33a for moving the dispensing part 31a from the origin position to the corresponding protrusion J12). It should be noted that by reducing the moving speed in the horizontal direction of the dispensing part 31a during scan, displacement of the peak positions relative to the position of the protrusion J12 shown in FIG. 13A can be reduced. However, by moving the dispensing part 31a at the same speed in detection in the Y-axis forward direction and in the Y-axis reverse direction, response lag of the capacitance sensor relative to the distance of movement in the Y-axis forward direction and response lag of the capacitance sensor relative to the distance of movement in the Y-axis reverse direction can be made substantially the same therebetween. Thus, the displacement amount between the peak position and the position of the protrusion J12 in detection in the Y-axis forward direction and the displacement amount between the peak position and the position of the protrusion J12 in detection in the Y-axis reverse direction can be made substantially the same therebetween. Therefore, by determining the middle position of the peak position in the Y-axis forward direction and the peak position in the Y-axis reverse direction, it is possible to accurately obtain the position of the protrusion J12. According to this method, even in a state where the moving speed in the horizontal direction of the dispensing part 31a during scan is increased, the position of the protrusion J12 can be accurately specified. Thus, the automatic position adjustment process can be efficiently performed.

Next, the CPU 301 controls the stepping motors 32a and 33a, to move the dispensing parts 31a to the obtained rough position. The CPU 301 further controls the stepping motor 34a, to lower the dispensing parts 31a until the lower ends of the nozzle parts 31b of the two dispensing parts 31a come into contact with the upper ends of the protrusions J12 of the position adjustment jig J1 (step S114). Accordingly, reference position information (the number of pulses of the stepping motor 34a for lowering, from a predetermined reference height, the dispensing parts 31a until the lower ends of the nozzle parts 31b come into contact with the upper ends of the protrusions J12 of the position adjustment jig J1) in the Z-axis direction of the dispensing parts 31a at the time when the lower ends of the nozzle parts 31b have come into contact with the upper ends of the protrusions J12 of the position adjustment jig J1 is obtained.

The CPU 301 stores the rough position information in the X-axis direction and the Y-axis direction and the reference position information in the Z-axis direction obtained as above, into the hard disk 304 (step S115).

Next, the CPU 301 determines whether rough position information at the last set place (i.e., the set place on the rear side of the reaction part 50) has been obtained (step S116). When the rough position information at the last set place has not been obtained (NO in step S116), the CPU 301 selects the next set place (step S117), and returns the process to step S102. It should be noted that, when the dispensing parts 31a are moved from one set place to the next set place, the dispensing parts 31a are moved without returning to the origin position but directly to the next set place. By repeating the above process, the rough position information at all the set places is obtained.

In step S116, when the rough position information at the last set place has been obtained (YES in step S116), the CPU 301 ends the simple position search process and returns the process to the automatic position adjustment process (main routine).

Next, the fine position search process will be described in detail. Also in the fine position search process, as in the simple position search process, the positions of the protrusions J12 to J42 are searched in order at the set places described above. FIG. 14 is a plan view of the inside of the sample processing apparatus 1 for explaining the order of position adjustment in the fine position search process. As shown in FIG. 14, in the fine position search process, the set place at the rear-most side of the tip setting part 40 to the set place at the front-most side are searched in order. Then, the set place of the reagent container setting part 20 is searched. Then, the set place of the sample container setting part 10 is searched. Then, the search place at the rear side and the search place at the front side of the reaction part 50 are searched in order. Then, finally, the search place of the tip disposal part 60 is searched. The circled numbers in FIG. 14 show the order of the search.

FIG. 15A and FIG. 15B are a flow chart showing the procedure of the fine position search process. In the fine position search process, first, the CPU 301 selects the first set place (i.e., the set place of the rear-most side of the tip setting part 40) (step S201). Then, the CPU 301 reads out, from the hard disk 304, rough position information and reference position information in the Z-axis direction of the selected set place. Then, the CPU 301 sets the fine search region SA2 by use of the rough position information (step S202).

The fine search region SA2 is set as a rectangular region of a predetermined size having the rough position at the center. As described above, the fine search region SA2 is a region smaller than the simple search region SA1.

Next, the CPU 301 controls the stepping motors 32*a* and 33*a*, to locate the two dispensing parts 31*a* at an X-direction fine search initial position of the selected search place (step S203). The X-direction fine search initial position is the position at the right front corner of the fine search region SA2.

Next, the CPU 301 controls the stepping motor 34*a* to locate the dispensing parts 31*a* at a position higher, by a predetermined distance (for example, 1 mm), than a reference height indicated by the read out reference position information in the Z-axis direction (step S204). This height is a height that is lower than the height of the dispensing parts 31*a* in the simple position search process (i.e., the distance between the lower end of each nozzle part 31*b* and the upper end of the protrusion J12 to J42 is shorter).

Next, the CPU 301 controls the stepping motor 32*a* to move the dispensing parts 31*a* in the X-axis forward direction at a predetermined speed (hereinafter, referred to as "fine search speed"). Then, the CPU 301 reads out detection values of the capacitance sensor 35 at a predetermined sampling interval (hereinafter, referred to as "fine search sampling interval") during this time. Then, the CPU 301 stores the detection values in the internal memory of the CPU 301 (step S205). It should be noted that the fine search speed is slower than the simple search speed. The fine search sampling interval is longer than the simple search sampling interval so as to perform the same number of samplings as that in the simple search. Thus, at each predetermined distance (hereinafter, referred to as "fine search sampling distance") in the X-axis direction determined by the fine search speed and the fine search sampling interval, the detection value of the capacitance sensor 35 is intermittently read out.

When the above scan has reached the left end of the fine search region SA2, the CPU 301 controls the stepping motor 32*a* to move the dispensing parts 31*a* in the X-axis reverse direction at the fine search speed. Then, the CPU 301 reads out detection values of the capacitance sensor 35 at a predetermined sampling interval during this time. Then, the CPU 301 stores the detection values in the internal memory of the CPU 301 (step S206). Thus, at each fine search sampling distance in the X-axis direction, the detection value of the capacitance sensor 35 is intermittently read out.

When the above scan has reached the right end of the fine search region SA2, the CPU 301 determines whether the search has been completed up to the rear end of the fine search region SA2 (step S207). When the search has not been completed up to the rear end of the fine search region SA2 (NO in step S207), the CPU 301 controls the stepping motor 33*a* to move the dispensing parts 31*a* rearward by a predetermined distance (step S208). Detection values of the capacitance sensor 35 during this movement rearward are not read out.

When the dispensing parts 31*a* have been moved rearward by the predetermined distance, the CPU 301 returns the process to step S205, to execute the process of step S205 (fine scan in the X-axis forward direction) and the process of S206 (fine scan in the X-axis reverse direction) again.

In step S207, when the search has been completed up to the rear end of the fine search region SA2 (YES in step S207), the CPU 301 shifts the process to step S209. In the present embodiment, the numbers of times of the fine scan in the X-axis forward direction and the X-axis reverse direction are three, respectively. However, the numbers of times of the fine scan in the X-axis forward direction and the X-axis reverse direction are not limited thereto.

As described above, the fine search speed is slower than the simple search speed, and the fine search sampling interval is longer than the simple search sampling interval. The fine search and the simple search are set such that the same number of samplings are performed as described above. However, since the fine search region SA2 is a region smaller than the simple search region SA1, the fine search sampling distance is shorter than the simple search sampling distance. Thus, in the fine position search process, compared with the simple position search process, position of the protrusion J12 to J42 is searched more finely.

After the last fine position search in the X-axis reverse direction has been completed, the dispensing parts 31*a* are moved to the origin position (step S209). In the search in the X-axis direction, with respect to the X-axis direction, the dispensing parts 31*a* have been moved in both of the forward direction and the reverse direction, but with respect to the Y-axis direction, the dispensing parts 31*a* have been moved only in one direction, i.e., rearward direction. Thus, there is a risk that a slight difference occurs between the position of the nozzle parts 31*b* held by CPU 301 and the actual position of the nozzle parts 31*b* in the Y-axis direction, due to influence and the like of backlash (gap in feed screws, gears, and the like). Therefore, by returning the dispensing parts 31*a* to the origin position after the search in the X-axis direction has been completed in the fine position search, it is possible to adjust the position of the nozzle parts 31*b* held by the CPU 301 and the actual position of the nozzle parts 31*b* with each other again. Accordingly, it becomes possible to perform more accurate position search in the subsequent search in the Y-axis direction. This step is omitted in the simple search in order to increase the search speed.

As described above, after the dispensing parts 31*a* are moved to the origin position, the dispensing parts 31*a* are located to the right front corner (hereinafter, referred to as "Y-direction fine search initial position") of the fine search region SA2 (step S210). In a state where the dispensing parts 31*a* are located at the Y-direction fine search initial position, the CPU 301 controls the stepping motor 33*a* to move the dispensing parts 31*a* in the Y-axis reverse direction at the fine search speed. Then, the CPU 301 reads out detection values of the capacitance sensor 35 at the fine search sampling interval during this time. Then, the CPU 301 stores the detections values in the internal memory of the CPU 301 (step S211). Thus, at each fine search sampling distance in the Y-axis direction, the detection value of the capacitance sensor 35 is intermittently read out.

When the above scan has reached the rear end of the fine search region SA2, the CPU 301 controls the stepping motor 33*a* to move the dispensing parts 31*a* in the Y-axis forward direction at the fine search speed. Then, the CPU 301 reads out detection values of the capacitance sensor 35 at a predetermined sampling interval during this time. Then, the CPU 301 stores the detection values in the internal memory of the CPU 301 (step S212). Thus, at each fine search sampling distance in the Y-axis direction, the detection value of the capacitance sensor 35 is intermittently read out.

When the above scan has reached the front end of the fine search region SA2, the CPU 301 determines whether the search has been completed up to the left end of the fine search region SA2 (step S213). When the search has not been completed up to the left end of the fine search region SA2 (NO in step S213), the CPU 301 controls the stepping motor 32a to move the dispensing parts 31a leftward by a predetermined distance (step S214). Detection values of the capacitance sensor 35 during this movement leftward are not read out.

When the dispensing parts 31a have been moved leftward by the predetermined distance, the CPU 301 returns the process to step S211, to execute the process of step S211 (fine scan in the Y-axis reverse direction) and the process of S212 (fine scan in the Y-axis forward direction) again.

In step S213, when the search has been completed to the left end of the fine search region SA2 (YES in step S213), the CPU 301 shifts the process to step S215. In the present embodiment, the numbers of times of fine scan in the Y-axis reverse direction and the Y-axis forward direction are three, respectively. However, the numbers of times of fine scan in the Y-axis reverse direction and the Y-axis forward direction are not limited thereto.

The CPU 301 integrates, for each position in the X-axis direction, detection values of capacitance obtained through the three times of fine scan in the X-axis forward direction, to obtain integrated capacitance in the X-axis forward direction. The CPU 301 integrates, for each position in the X-axis direction, detection values of capacitance obtained through the three times of fine scan in the X-axis reverse direction, to obtain integrated capacitance in the X-axis reverse direction. The CPU 301 integrates, for each position in the Y-axis direction, detection values of capacitance obtained through the three times of fine scan in the Y-axis reverse direction, to obtain integrated capacitance in the Y-axis reverse direction. The CPU 301 integrates, for each position in the Y-axis direction, detection values of capacitance obtained through the three times of fine scan in the Y-axis forward direction, to obtain integrated capacitance in the Y-axis forward direction. Then, the CPU 301 stores, in the internal memory of the CPU 301, the integrated capacitances in the X-axis forward direction, the X-axis reverse direction, the Y-axis forward direction, and the Y-axis reverse direction (step S215). This process is the same as the process of step S111 in the simple position search process.

Next, in step S216, the CPU 301 specifies the position in the X-axis direction of the peak of the integrated capacitance in the X-axis forward direction, and the position in the X-axis direction of the peak of the integrated capacitance in the X-axis reverse direction. Then, the CPU 301 determines the middle position (average value of coordinates in the X-axis direction) in the X-axis direction of both peaks. The CPU 301 obtains this middle position information as reference position information in the X-axis direction (the number of pulses of the stepping motor 32a for moving each dispensing part 31a from the origin position to the corresponding protrusion J12). Similarly, in step S216, the CPU 301 specifies the position in the Y-axis direction of the peak of the integrated capacitance in the Y-axis forward direction, and the position in the Y-axis direction of the peak of the integrated capacitance in the Y-axis reverse direction. Then, the CPU 301 determines the middle position (average value of coordinates in the Y-axis direction) in the Y-axis direction of both peaks. The CPU 301 obtains this middle position information as reference position information in the Y-axis direction (the number of pulses of the stepping motor 33a for moving the dispensing part 31a from the origin position to the corresponding protrusion J12).

Next, the CPU 301 determines whether reference position information at the last set place (i.e., the set place of the tip disposal part 60) has been obtained (step S217). When the reference position information at the last set place has not been obtained (NO in step S217), the CPU 301 selects the next set place (step S218), and returns the process to step S202. It should be noted that, when the dispensing parts 31a are moved from one set place to the next set place, the dispensing parts 31a are moved without returning to the origin position but directly to the next set place. By repeating the above process, the reference position information at all the set places is obtained.

In step S217, when the reference position information at the last set place has been obtained (YES in step S217), the CPU 301 ends the fine position search process and returns the process to the automatic position adjustment process (main routine).

As described in detail above, in the sample processing apparatus 1 according to the present embodiment, while the dispensing parts 31a are being horizontally moved above the position adjustment jigs J1 to J4 without colliding with the position adjustment jigs J1 to J4 in the front-rear direction or the left-right direction, change in capacitance detected by the capacitance sensor 35 is used to set the reference position of the dispensing parts 31a. Thus, deformation, damage, and the like of the dispensing parts 31a can be prevented.

Other Embodiments

In the embodiment described above, a configuration has been described in which: the position adjustment jigs J1 to J4 are attached to the sample container setting part 10, the reagent container setting part 20, the tip setting part 40, the reaction part 50, and the tip disposal part 60; and based on change in capacitance detected by the capacitance sensor 35, while the dispensing parts 31a are being horizontally moved above the position adjustment jigs J1 to J4, the positions of the protrusions J12 to J42 provided in the position adjustment jigs J1 to J4 are searched to be used as reference positions. Other than this, however, another configuration may be employed in which: protrusions that are made of conductive material and that are not detachable are directly provided at positions, for example, near the sample container setting part 10, the reagent container setting part 20, the tip setting part 40, the reaction part 50, and the tip disposal part 60 of the housing of the sample processing apparatus 1, and the dispensing parts 31a are moved above these protrusions; and based on change in capacitance detected during that time, the positions of the protrusions are searched, and these positions are used as reference positions.

In the embodiment described above, a configuration has been described in which: in the adjustment step after the sample processing apparatus 1 has been produced, the sample processing apparatus 1 executes the automatic position adjustment process. Other than this, however, another configuration can be employed in which: after the sample processing apparatus 1 has been provided to a user, periodically, for example, immediately after activation of the sample processing apparatus 1 every day, or once a week, the sample processing apparatus 1 executes the automatic position adjustment process. Accordingly, even when abnormality in positioning has occurred due to displacement or the like in the position of the dispensing parts 31a while the user is using the sample processing apparatus 1, the sample processing apparatus 1 can easily have the normal positioning accuracy again.

In the embodiment described above, a configuration has been described in which: the protrusions J12 to J42 are provided to the position adjustment jigs J1 to J4; change is caused, by the presence of the protrusions J12 to J42, in the capacitance that is detected while the dispensing parts 31a are being horizontally moved above the position adjustment jigs J1 to J4; and the positions of the protrusions J12 to J42 are searched based on the change. Other than this, however, another configuration can be employed in which: instead of the protrusions J12 to J42, recesses are formed in the position adjustment jigs, or portions made of insulating material are provided in a part of the position adjustment jigs, whereby change is caused in the capacitance that is detected while the dispensing parts 31a are being horizontally moved above the position adjustment jigs J1 to J4; and based on this change, the positions of the recesses or the portions made of the insulating material are searched.

In the embodiment described above, a configuration has been described in which: in the automatic position adjustment process, position search of the protrusions J12 to J42 is performed in two stages of the simple position search process and the fine position search process. Other than this, however, another configuration may be employed in which: for example, position search of the protrusions J12 to J42 is performed once; and the positions obtained by this one search are determined as reference positions.

In the embodiment described above, a configuration has been described in which: in each of the simple position search process and the fine position search process, scan is performed a plurality of times (three times) in each of the X-axis direction and the Y-axis direction; integrated capacitance is obtained by integrating, at each position in each of the X-axis direction and the Y-axis direction, the detection values of capacitance obtained through the plurality of times of scan; and based on the integrated capacitances, the positions of the protrusions J12 to J42 are searched. Other than this, however, another configuration can be employed in which: among detection values of capacitance obtained through a plurality of times of scan performed in each of the X-axis direction and the Y-axis direction, detection values of capacitance of one scan are selected; and based on the selected detection values of capacitance, the positions of the protrusions J12 to J42 are searched. Alternatively, the scan in the X-axis direction and the scan in the Y-axis direction are not performed independently, but instead, the scan in the X-axis direction and the scan in the Y-axis direction may be performed alternately. For example, the dispensing part 31a may be moved in the horizontal plane in a zigzag shape to perform scanning, or may be moved in a spiral shape to perform scanning.

In the embodiment described above, a configuration has been described in which: in the automatic position adjustment process, the pipette tip C is not attached to each nozzle part 31b to which the pipette tip C is attachable/detachable; and the nozzle part 31b is used as a probe of the capacitance sensor 35. Other than this, however, another configuration can be employed in which: the nozzle part 31b having the pipette tip C attached thereto is used as a probe to execute the automatic position adjustment process. Alternatively, another configuration may be employed in which: the capacitance sensor is connected to an aspirator which is not configured to have the pipette tip C to be detachably attached, but which is provided with an aspiration tube to be used without being detached; and the aspiration tube is used as a probe, to execute the automatic position adjustment process.

In the embodiment described above, in the automatic position adjustment process, the positions of the protrusions J12 to J42 provided in the position adjustment jigs J1 to J4 are searched by use of the capacitance sensor 35. However, another sensor such as a pressure sensor, an ultrasonic sensor, an optical sensor, or the like may be used to search, in a non-contact manner, the positions of the protrusions J12 to J42 provided in the position adjustment jigs J1 to J4. By using such a sensor also as the sensor that detects whether the dispensing part 31a or the pipette tip C comes into contact with the liquid surface as in the embodiment described above, it is possible to contribute to downsizing of the apparatus.

In the embodiment described above, a configuration has been described in which: in the simple position search in the X-axis direction, after the scan in the X-axis forward direction has been performed, the scan in the X-axis reverse direction is performed; in the simple position search in the Y-axis direction, after the scan in the Y-axis forward direction has been performed, the scan in the Y-axis reverse direction is performed; in the fine position search in the X-axis direction, after the scan in the X-axis forward direction has been performed, the scan in the X-axis reverse direction is performed; and in the fine position search in the Y-axis direction, after the scan in the Y-axis reverse direction has been performed, the scan in the Y-axis forward direction is performed. However, another configuration may be employed in which: in each of the simple position search and the fine position search, after the scan in the X-axis forward direction has been performed, the scan in the X-axis reverse direction is performed; and after the scan in the Y-axis forward direction has been performed, the scan in the Y-axis reverse direction is performed. In the simple position search, either the forward direction or the reverse direction may be scanned first, and similarly, in the fine position search, either the forward direction or the reverse direction may be scanned first. The order of the scan direction may be reversed between the simple position search and the fine position search at one set place, and the order of the scan direction may not be reversed between the simple position search and the fine position search in another set place.

In the embodiment described above, the sample processing apparatus 1 is a nucleic acid amplification detecting apparatus. Other than this, however, in a sample processing apparatus, other than a nucleic acid amplification detecting apparatus, that includes an aspirator such as a blood cell analyzer (blood cell counter), a urine particle analyzer, a blood coagulation measuring apparatus, an immune analyzer, a biochemical analyzer, a smear preparing apparatus, or the like, the automatic position adjustment of the aspirator can be performed.

What is claimed is:

1. A method for adjusting a position of an aspirator in a sample processing apparatus, the sample processing apparatus comprising the aspirator configured to aspirate a sample or a reagent from a container, a capacitance sensor connected to the aspirator and a container setting part configured to have a container containing a liquid set thereon, the method comprising:

detachably inserting a position adjustment part which is electrically conductive into at least one of holding holes of the container setting part, wherein the position adjustment part comprises a flat top face and a protrusion protruding upward from a part of the flat top face;

moving the aspirator above the position adjustment part so that a lower end of the aspirator moves horizontally in a predefined quadrangular searching region having four sides without contacting the position adjustment part;

obtaining capacitance detected by the capacitance sensor while moving the aspirator without contacting the position adjustment part;

searching a position of the protrusion of the position adjustment part inserted into the at least one of the holding holes based on change in the obtained capacitance while the aspirator is moving above the position adjustment part; and setting reference position information indicating a reference position of the aspirator based on the searched position, wherein the step of moving the aspirator above the position adjustment part further comprises:

reciprocating the lower end of the aspirator along each of a plurality of first parallel routes between two opposing sides of the searching region; and reciprocating the lower end of the aspirator along each of a plurality of second parallel routes between the other two opposing sides of the searching region.

2. A sample processing apparatus comprising:

a liquid aspirator configured to aspirate a liquid from a container selected from among a plurality of containers;

a container setting part having holding holes configured to insert the plurality of containers;

a capacitance sensor connected to the aspirator to detect change in capacitance in a non-contact manner;

a movement mechanism connected to the liquid aspirator to move the liquid aspirator;

a position adjustment part which is electrically conductive and configured to be detachably inserted into at least one of the holding holes, wherein the position adjustment part comprises a flat top face and a protrusion protruding upward from a part of the flat top face; and a controller programmed to perform operations comprising:

moving the aspirator above the position adjustment part so that a lower end of the aspirator moves horizontally in a predefined quadrangular searching region having four sides without contacting the position adjustment part;

obtaining capacitance detected by the capacitance sensor while moving the aspirator without contacting the position adjustment part;

searching a position of the protrusion of the position adjustment part inserted into the at least one of the holding holes based on change in capacitance detected by the capacitance sensor while the liquid aspirator is moving above the position adjustment part; and setting reference position information including a reference position of the liquid aspirator based on the searched position;

wherein the moving operation is performed by:

reciprocating the lower end of the aspirator along each of a plurality of first parallel routes between two opposing sides of the searching region; and reciprocating the lower end of the aspirator along each of a plurality of second parallel routes between the other two opposing sides of the searching region.

3. The sample processing apparatus of claim 2, wherein the position adjustment part is configured such that capacitance detected by the capacitance sensor when the capacitance sensor is located above the protrusion corresponding to the reference position is different from capacitance detected by the capacitance sensor when the capacitance sensor is located above another portion.

4. The sample processing apparatus of claim 2, wherein the capacitance sensor is configured to detect change in capacitance when the liquid aspirator has come into contact with a liquid surface.

5. The sample processing apparatus of claim 2, wherein the first parallel routes are parallel to a first horizontal direction and the second parallel routes are parallel to a second horizontal direction perpendicular to the first horizontal direction, the controller is programmed to perform operations comprising:

specifying a first horizontal direction component value of the reference position based on change in capacitance detected by the capacitance sensor while the liquid aspirator is moving in the first horizontal direction;

specifying a second horizontal direction component value of the reference position based on change in capacitance detected by the capacitance sensor while the liquid aspirator is moving in the second horizontal direction; and setting the specified first horizontal direction component value and the specified second horizontal direction component value as the reference position information.

6. The sample processing apparatus of claim 5, wherein the controller is programmed to perform operations comprising:

controlling the movement mechanism such that the liquid aspirator moves along each of the first parallel routes in the first horizontal direction and specifying a first horizontal direction component value of the reference position based on change in capacitance detected by the capacitance sensor while the liquid aspirator is moving in the first horizontal direction a plurality of times; and controlling the movement mechanism such that the liquid aspirator moves along each of the second parallel routes in the second horizontal direction, and specifying a second horizontal direction component value of the reference position based on change in capacitance detected by the capacitance sensor while the liquid aspirator is moving in the second horizontal direction a plurality of times.

7. The sample processing apparatus of claim 6, wherein the controller is programmed to perform operations comprising:

integrating capacitance detected by the capacitance sensor while the liquid aspirator is moving in the first horizontal direction the plurality of times, at each of a plurality of positions in the first horizontal direction, and specifying a first horizontal direction component value of the reference position based on each integrated value; and integrating capacitance detected by the capacitance sensor while the liquid aspirator is moving in the second horizontal direction the plurality of times, at each of a plurality of positions in the second horizontal direction, and specifying a second horizontal direction component value of the reference position based on each integrated value.

8. The sample processing apparatus of claim 2, wherein the controller is programmed to perform operations comprising executing:
   a simple search process in which the movement mechanism is controlled such that the liquid aspirator horizontally moves in a first quadrangular searching region as the searching region, and in which a rough position of the reference position is specified based on capacitance detected by the capacitance sensor while the liquid aspirator is horizontally moving in the first searching region; and
   a fine search process in which the movement mechanism is controlled such that the liquid aspirator horizontally moves in a second quadrangular searching region set within the first searching region, and in which a fine position of the reference position is specified based on capacitance detected by the capacitance sensor while the liquid aspirator is horizontally moving in the second searching region.

9. The sample processing apparatus of claim 8, wherein the controller is programmed to perform operations comprising:
   controlling, in the simple search process, the movement mechanism such that the liquid aspirator horizontally moves in the first search region; and
   controlling, in the fine search process, the movement mechanism such that the liquid aspirator horizontally moves in the second search region which is smaller than the first search region.

10. The sample processing apparatus of claim 8, wherein the controller is programmed to perform operations comprising:
   controlling, in the simple search process, the movement mechanism such that the liquid aspirator moves above the position adjustment part by a first distance thereabove, and
   controlling, in the fine search process, the movement mechanism such that the liquid aspirator moves above the position adjustment part by a second distance thereabove, the second distance being shorter than the first distance.

11. The sample processing apparatus of claim 8, wherein the controller is programmed to perform operations comprising:
   executing, after the simple search process, a height setting process in which a reference height of the liquid aspirator is set by moving the liquid aspirator in a vertical direction to bring the liquid aspirator into contact with the position adjustment part; and
   determining a height of the liquid aspirator in the fine search process based on the reference height set in the height setting process to execute the fine search process.

12. The sample processing apparatus of claim 10, wherein each second distance of first parallel routes of the second searching region is shorter than each first distance of first parallel routes of the first searching region.

13. The sample processing apparatus of claim 2, wherein the first parallel routes are substantially equally spaced and the second parallel routes are substantially equally spaced.

14. The sample processing apparatus of claim 2, wherein the liquid aspirator has a nozzle part configured to detachably attach a pipette tip, and
the controller is programmed to perform the moving the aspirator above the position adjustment part before the pipette tip is attached to the nozzle part.

15. The method of claim 1, wherein
the first parallel routes are substantially equally spaced and the second parallel routes are substantially equally spaced.

16. The sample processing apparatus of claim 1, wherein
the liquid aspirator has a nozzle part configured to detachably attach a pipette tip, and
the moving the aspirator above the position adjustment part is performed before the pipette tip is attached to the nozzle part.

\* \* \* \* \*